United States Patent
Dirisio

(10) Patent No.: US 11,051,775 B2
(45) Date of Patent: Jul. 6, 2021

(54) COLLAPSIBLE COLUMN MOVEMENT APPARATUS FOR MOBILE X-RAY DEVICE

(71) Applicant: CARESTREAM HEALTH, INC., Rochester, NY (US)

(72) Inventor: Anthony Dirisio, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 219 days.

(21) Appl. No.: 16/409,982

(22) Filed: May 13, 2019

(65) Prior Publication Data

US 2019/0357863 A1    Nov. 28, 2019

Related U.S. Application Data

(60) Provisional application No. 62/674,745, filed on May 22, 2018.

(51) Int. Cl.
*A61B 6/00* (2006.01)

(52) U.S. Cl.
CPC ............ *A61B 6/4405* (2013.01); *A61B 6/447* (2013.01); *A61B 6/4452* (2013.01)

(58) Field of Classification Search
CPC ...... A61B 6/4405; A61B 6/4452; A61B 6/447
See application file for complete search history.

(56) References Cited

U.S. PATENT DOCUMENTS 8,568,028 B2    10/2013    Wendlandt et al.
2016/0199013 A1*    7/2016    Moreno Vallejo ... A61B 6/4405
                                                            378/194

\* cited by examiner

*Primary Examiner* — Chih-Cheng Kao

(57) ABSTRACT

A mobile radiography apparatus with a portable transport frame has a sectioned vertical column mounted on the transport frame. The sectioned vertical column defines a vertical axis and has a vertically fixed base section and an upper section that is movable with respect to the base section along the vertical axis. Cable and pulley systems are coupled to the vertical column sections and/or the transport frame. A boom is coupled to the movable section for positioning an x-ray source attached to the boom.

17 Claims, 23 Drawing Sheets

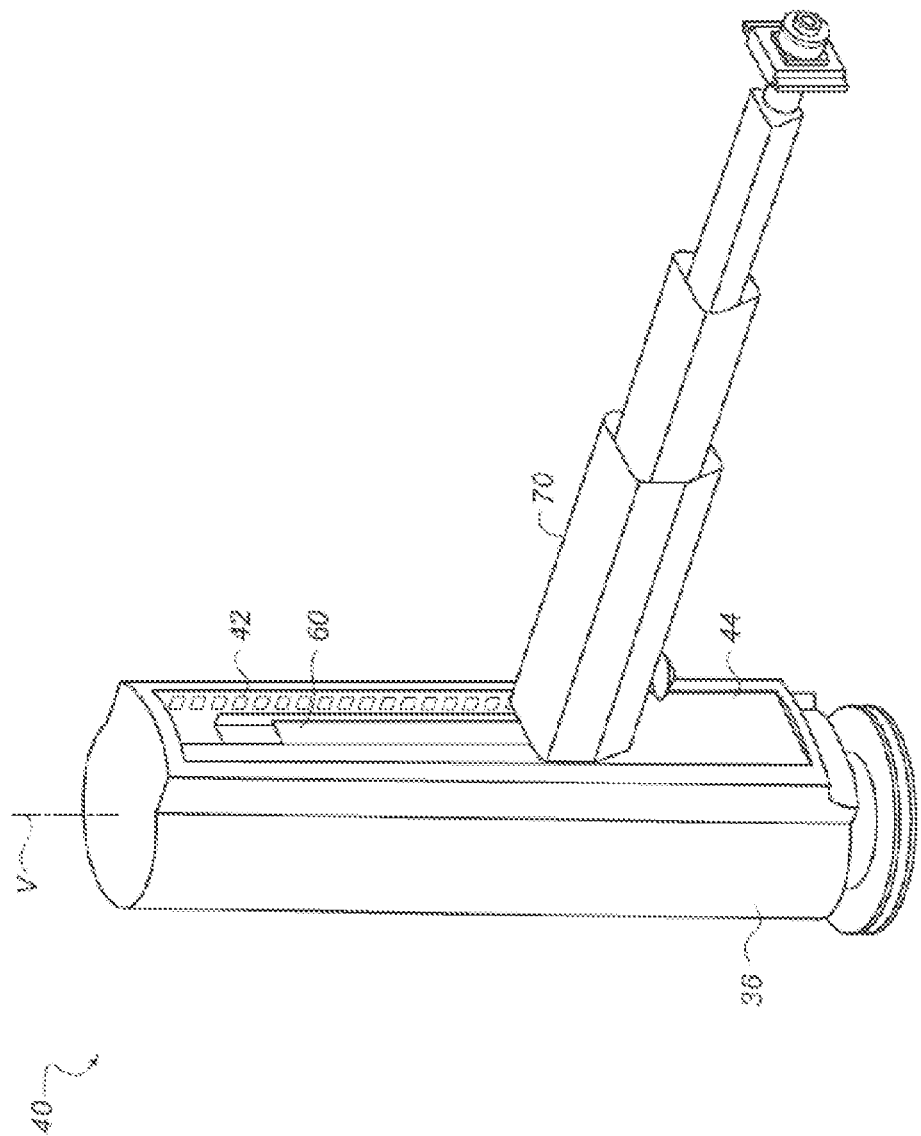

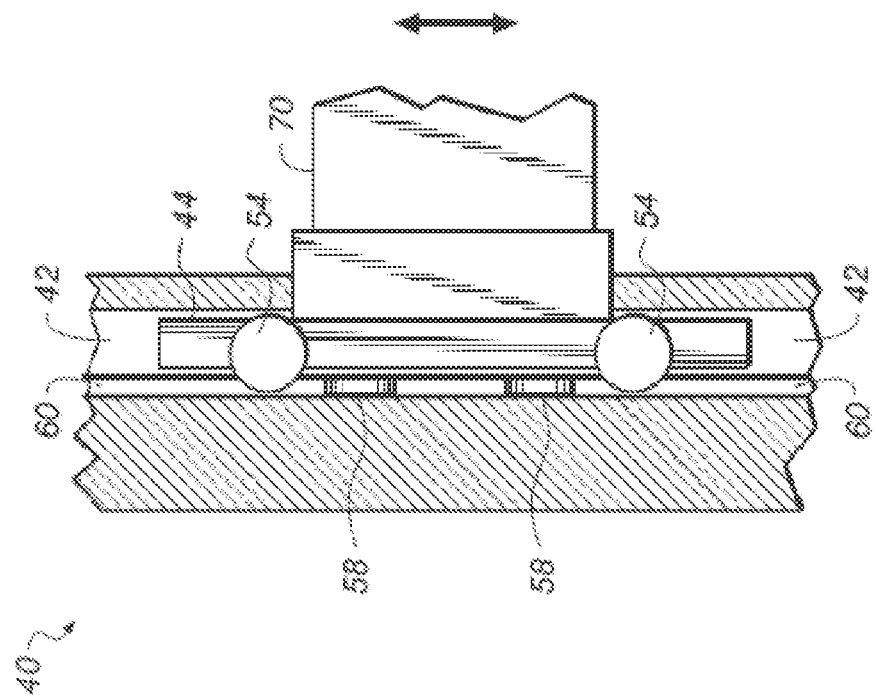
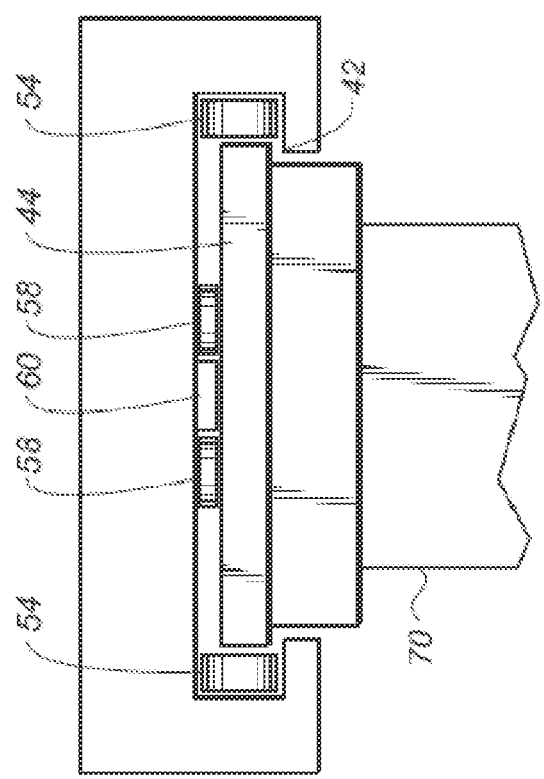
FIG. 14A
FIG. 14B

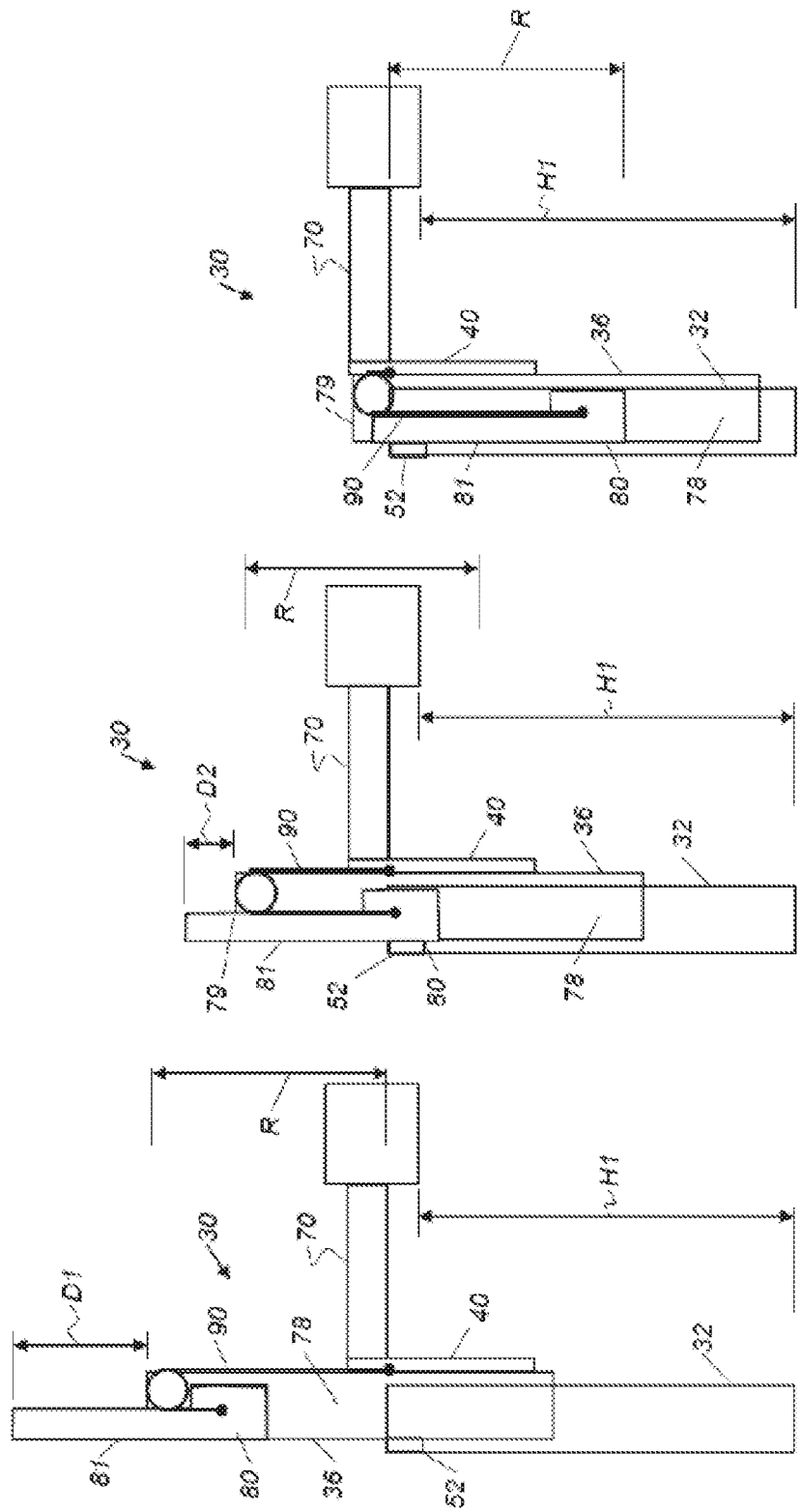

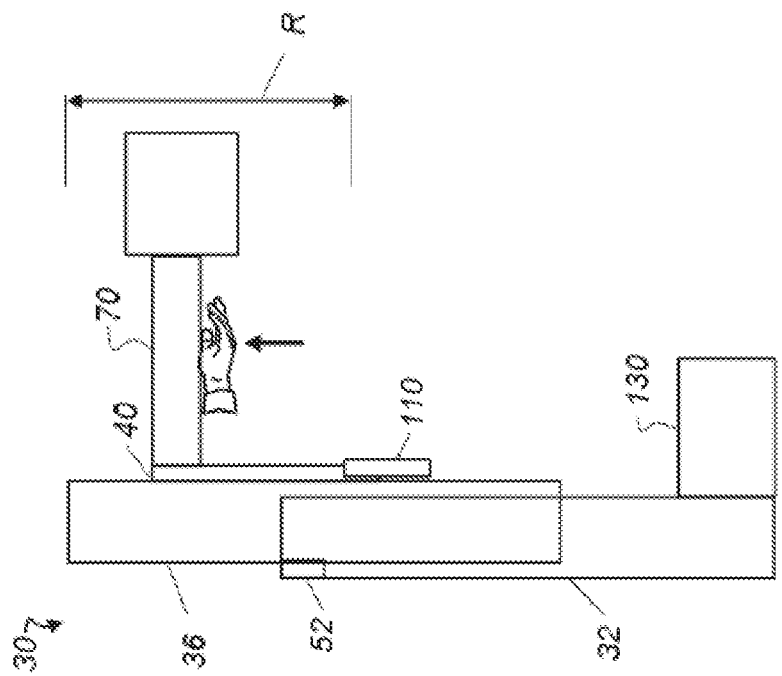
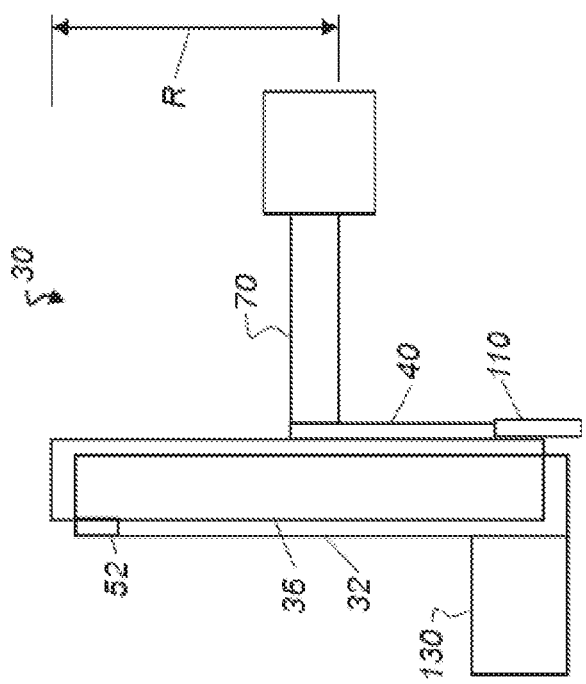
FIG. 19A
FIG. 19B

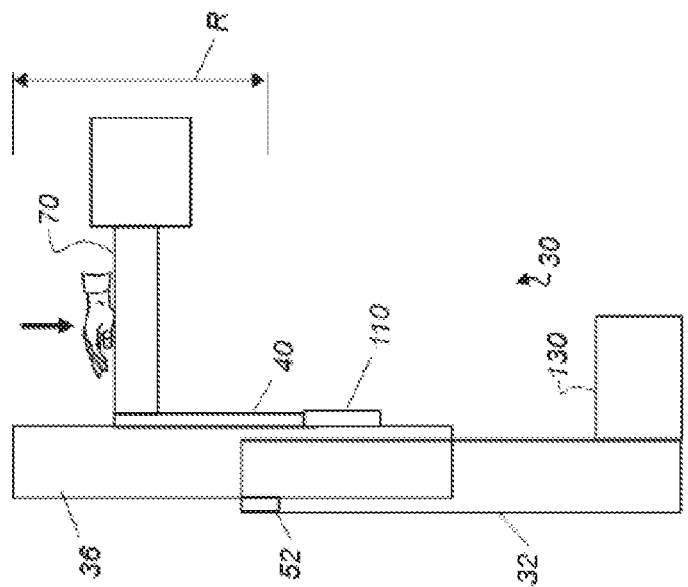
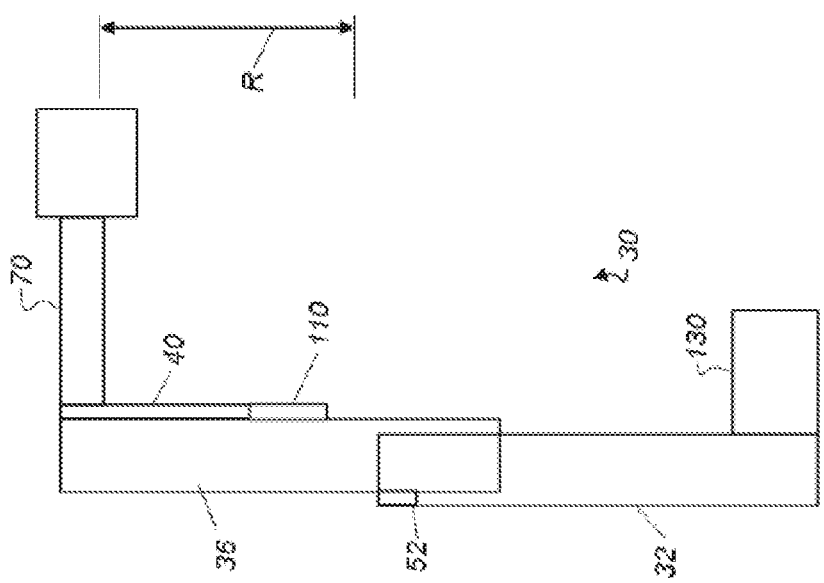

COLLAPSIBLE COLUMN MOVEMENT APPARATUS FOR MOBILE X-RAY DEVICE

CROSS REFERENCE TO RELATED APPLICATIONS

This application claims priority to U.S. Patent Application Ser. No. 62/674,745, filed May 22, 2018, in the name of Anthony Dirisio, and entitled "COLLAPSIBLE COLUMN MOVEMENT APPARATUS FOR MOBILE X-RAY DEVICE", which is hereby incorporated by reference herein in its entirety.

FIELD OF THE INVENTION

The present invention relates generally to the field of radiography and in particular to portable radiographic imaging apparatus. More specifically, the invention relates to column height adjustment in a mobile radiography apparatus having a collapsible support column with an x-ray boom of adjustable height.

BACKGROUND OF THE INVENTION

Mobile x-ray apparatus are of particular value in intensive care unit (ICU) and other environments where timely acquisition of a radiographic image is important. Because it can be wheeled around the ICU or other area and brought directly to the patient's bedside, a mobile x-ray apparatus allows an attending physician or clinician to have recent information on the condition of a patient and helps to reduce the risks entailed in moving patients to stationary equipment in the radiological facility.

The perspective view of FIG. 1 shows an example of a conventional mobile x-ray apparatus that can be employed for computed radiography (CR) and/or digital radiography (DR). A mobile radiography unit 600 has a frame 620 that includes a display 610 for display of obtained images and related data and a control panel 612 with a keyboard that allows instruction entry for storing, transmitting, modifying, and printing of the obtained image.

For mobility, unit 600 has one or more wheels 615 and one or more handle grips 625, typically provided at waist-, arm-, or hand-level, that help to guide unit 600 to its intended location. A self-contained battery pack typically provides source power, eliminating the need for operation near a power outlet.

Mounted to frame 620 is a columnar support member 635 that supports an x-ray source 640, also termed an x-ray tube, tube head, or generator mounted on a boom 70, more simply termed a boom 70. In the embodiment shown, support member 635 has a vertical column 64 of fixed height. Boom 70 extends outward a variable distance from support member 635 and translates up and down column 64 to the desired height for obtaining the image. Boom 70 may extend outward by a fixed distance or may be extendible over a variable distance. Height settings for the x-ray source 640 can range from low height for imaging feet and lower extremities to shoulder height and above for imaging the upper body portions of patients in various positions. In other conventional embodiments, the support member for the x-ray source is not a fixed column, but is rather an articulated member that bends at a joint mechanism to allow movement of the x-ray source over a range of vertical and horizontal positions.

One concern that must be addressed in design of the support member relates to ease of positioning of the x-ray source mounted on its boom. For ease of operation under varying conditions, the technician should be able to easily position and orient the x-ray source without requiring both hands, without the need of additional tools, and without needing help from nearby personnel. This includes moving the x-ray source from its docked position used in transport to an imaging position. The mechanical problem of providing ease of positioning is complicated by the weight of the x-ray source and by its extension outward from the vertical axis, While the conventional mobile x-ray apparatus described as unit 600 provides portable imaging capability in a number of applications, however, there are drawbacks to existing designs that can make these devices difficult to deploy in some circumstances. One of the problems common to conventional designs is due, in part, to the relative mobility and range of motion of the mobile x-ray apparatus that is needed.

The side view of FIG. 2 shows a significant problem that occurs when transporting a mobile radiography system, shown as a mobile radiography unit 62 that uses a fixed vertical structure, column 64. Boom 70 that provides transport of x-ray source 68, normally extended outward from unit 62 when in its imaging position, is folded back toward a technician 66 for transport. This transport position helps to protect the x-ray source from damage or from causing an obstruction during movement. Column 64, however, obstructs the view of technician 66 when moving the unit from one place to another, so that objects that are near the front edge of unit 62 or directly in front of the unit cannot readily be seen. The technician is required to peer around the column during transport and can be more prone to colliding or bumping against other equipment or obstacles in the hospital ward or other location. The fixed vertical column 64 may also present difficulties when passing or moving alongside accessory equipment, furniture, or patient support equipment. With obstructed vision, the technician must move slowly, impacting productivity and response time. Accidents and mishaps are more likely.

One type of solution for alleviating the visibility and mobility problems described with reference to FIG. 2 is to provide a collapsible column 64, as described in commonly assigned U.S. Pat. No. 8,568,028. Making column 64 collapsible, such as using a telescopic column design, not only allows improved visibility during movement of the mobile radiography unit 62, but also provides a more favorable weight distribution that is more compact and has a lowered center of gravity, facilitating movement of the unit by the technician from room to room.

While the collapsible column has advantages over fixed column height, however, a number of problems remain to be solved. One area of particular interest relates to boom movement for height adjustment. Because both the column height and boom height are adjustable, some amount of coordination is useful to help make it more natural to switch between various height positions, preferably so that the technician can concentrate attention on obtaining the best setup conditions for exposure without excessive concern for setting or adjusting column height relative to boom height.

Thus, there is a need for improvements in mobile x-ray apparatus design that allow ease of height adjustment of a collapsible column relative to the height of its boom transport mechanism.

SUMMARY OF THE INVENTION

An object of the present invention is to advance the art of mobile radiography. Another object of the present invention is to address the need for a mobile radiography unit that allows ease of movement of the boom assembly between vertical positions.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

In one embodiment, the present invention can provide a mobile radiography apparatus comprising: a portable transport frame; a sectioned vertical column mounted on the frame and defining a vertical axis and comprising a base section having a first vertical position relative to the vertical axis and at least one movable section that is translatable to a variable vertical position along the vertical axis; a counterbalance apparatus coupled to the at least one movable section of the vertical column, and with or without an actuator that is energizable to translate the at least one movable section along the vertical axis; a boom supporting an x-ray source and coupled to the at least one movable section for vertical displacement of the boom to a height position. A height sensing element may be included that provides a signal indicative of the height position of the boom. One or more column cable and pulley systems, including the counterbalance apparatus, comprises a column cable having a first end attached to the boom and a second end attached to the base section, which cable and pulley system mechanically assists a user to adjust a height of the boom and x-ray source.

In one embodiment, the present invention can provide a mobile radiography apparatus comprising a portable transport frame; a sectioned vertical column mounted on the frame and defining a vertical axis and comprising a base section having a fixed vertical position relative to the vertical axis and a movable section that is translatable to a variable vertical position along the vertical axis, a counterbalance apparatus coupled to the movable section of the vertical column, and comprising a tension force adjustment element in the transport frame. A boom apparatus supports an x-ray source and is movably coupled to the movable section for vertical displacement of the boom apparatus to a height position within a range of height positions along the movable section. One or more cable and pulley systems within the vertical column and/or the transport frame interacts with the counterbalance apparatus to mechanically assist a user to adjust a height of the boom apparatus and x-ray source.

In one embodiment, the present invention can provide a method for setting up a portable radiographic unit for an exposure, comprising mounting a sectioned vertical column on a portable transport frame, wherein the column defines a vertical axis and comprises a base section having a first vertical position relative to the vertical axis and at least one movable section that is vertically translatable to extend the vertical column along the vertical axis; coupling a boom apparatus supporting an x-ray source to the at least one movable section for vertical displacement of the boom apparatus to a height position; and responding to an operator urging to adjust the height of the boom apparatus for the exposure by translating at least the boom apparatus and, in certain instances, the movable section along the vertical axis. One or more cable and pulley systems within the vertical column and/or the portable transport frame mechanically assist a user to adjust a height of the boom and x-ray source.

In another embodiment, the present invention can provide a method for setting up a portable radiographic unit for an exposure, comprising providing a sectioned vertical column mounted on a portable transport frame, wherein the column defines a vertical axis and comprises a base section having a fixed vertical position relative to the vertical axis and a movable section that is translatable to a variable vertical position along the vertical axis; coupling a boom apparatus supporting an x-ray source to the movable section for vertical displacement of the boom apparatus to a height position, wherein the boom apparatus is movably displaceable vertically over a range that extends along at least a portion of the movable section. One or more cable and pulley systems within the vertical column and/or the portable transport frame mechanically assist a user to adjust a height of the boom and x-ray source.

In another embodiment, a mobile radiography system includes a transport frame having wheels for rolling the system to a patient bedside. A transport frame housing encloses at least a portion of the system. A sectioned vertical column is mounted on the rollable transport frame and includes a base section supported by and attached to the transport frame, which base section is rotatable, relative to the transport frame, about a vertical axis while remaining vertically stationary with respect to the transport frame. A movable upper section of the vertical column is coupled to the base section and is movable parallel to the vertical axis and relative to the base section. A boom having a first end attached to the movable upper section, and extending transversely therefrom, includes an x-ray source attached to a second end opposite the first end. The boom is configured to move as a unit vertically along a length of the movable upper section. One or more cable and pulley systems within the sectioned vertical column and/or within the transport frame assist a user to adjust a height of the boom and the x-ray source attached thereto.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 13 is a perspective view showing the boom transport on the upper section of the collapsible column, with the transport in a lower position.

FIG. 14A is a top view showing the carriage mechanism of the boom transport in one embodiment.

FIG. 14B is a side view showing the carriage mechanism of the boom transport in the FIG. 24A embodiment.

FIGS. 17A, 17B, and 17C are schematic views that show a number of possible combinations for achieving the same height for the boom apparatus using an embodiment with an elongated counterweight.

FIG. 19A is a block diagram showing the column in collapsed condition with the boom apparatus near the bottom of its travel path.

FIG. 19B is a block diagram showing the column extended with the boom apparatus traveling upward along its travel path.

FIG. 19C is a block diagram showing the column in fully extended condition with the boom apparatus near a top of its travel path.

FIG. 19D is a block diagram showing the column extended with the boom apparatus traveling downward along its travel path.

DETAILED DESCRIPTION OF THE INVENTION

Figure 1:
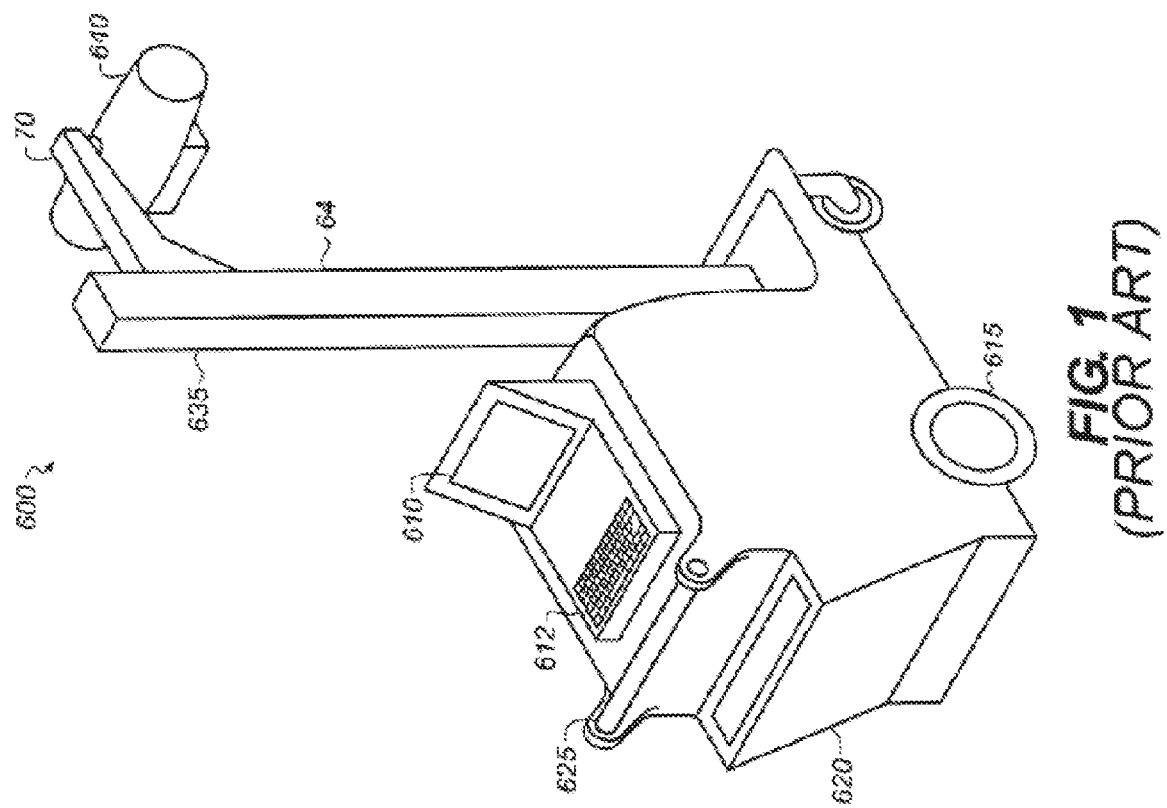
FIG. 1 shows a perspective view of a conventional mobile radiography unit using a fixed length vertical column for positioning the x-ray source.
Figure 2:
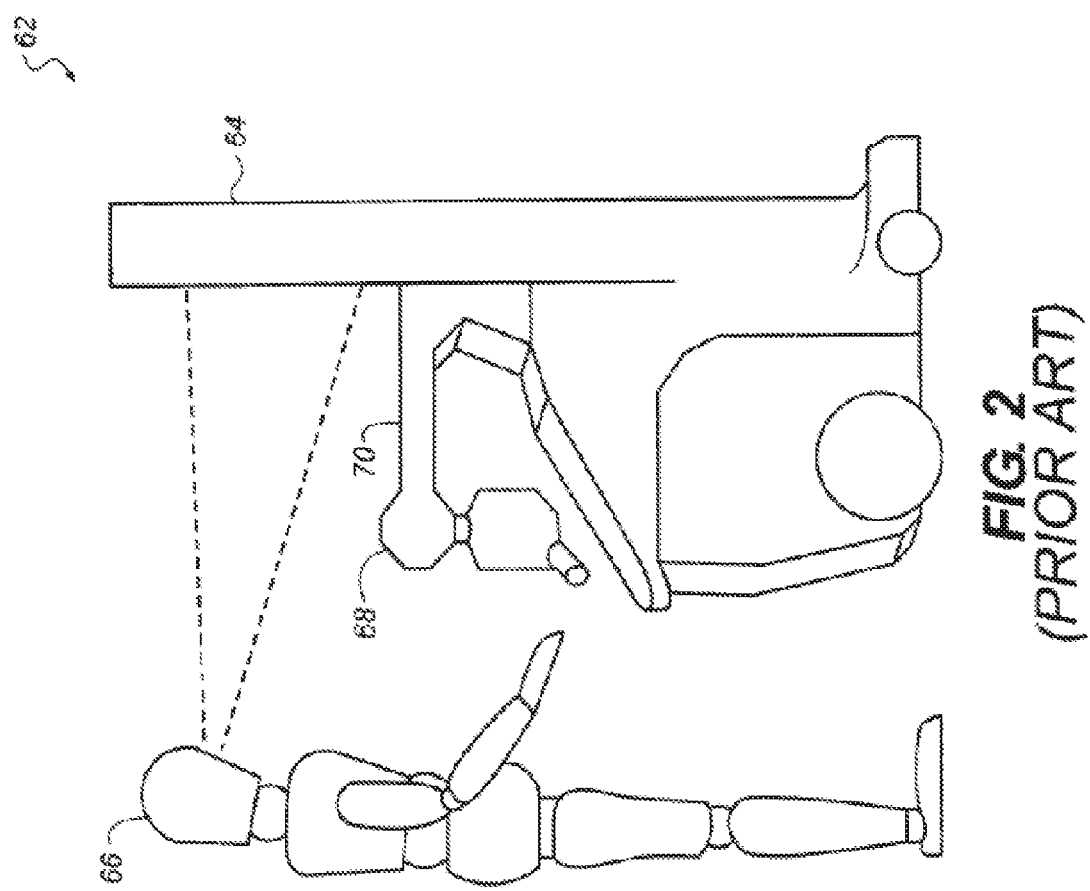
FIG. 2 shows a side view of a conventional mobile radiography unit with a fixed vertical column for positioning the x-ray source.

Apparatus and methods of the present invention address the need for a radiography unit that can be readily rolled from one place to another within a treatment facility, without the physical or visual obstruction that is common to many types of conventional mobile radiography equipment that use a vertical column. As noted previously, the x-ray source of such a system must allow elevation over a wide vertical range of motion, from heights near or above shoulder level for adults to very low elevations near the ankle or foot. One way to achieve this range of movement is the use of a jointed support member, as described previously. A somewhat simpler mechanical design is the use of a stationary vertical column as was shown in FIGS. 1 and 2, with the x-ray source mounted on a boom that extends outward horizontally from the column and travels vertically up and down the column. Two degrees of freedom are needed for boom 70 movement relative to the vertical column: translation along the vertical direction, that is, along the vertical axis, and rotation about the vertical axis. Boom 70 typically also extends to a variable horizontal length in a direction relative to the vertical axis, although it should be noted that a boom of fixed length could be used in a mobile radiography apparatus of the present invention.

Figure 3:
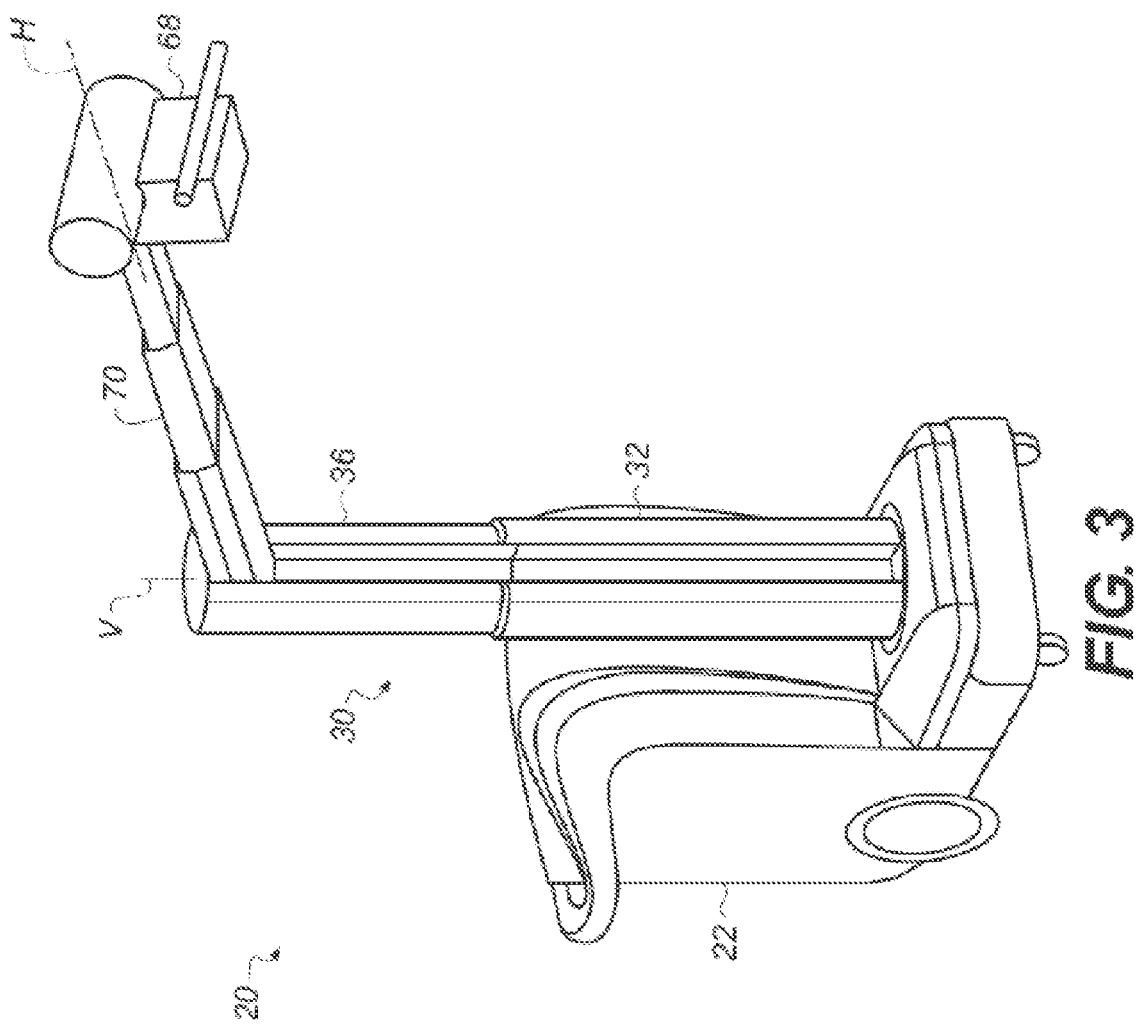
FIG. 3 shows a perspective view of a mobile radiography unit with a sectioned vertical column according to one embodiment of the present invention.
Figure 4:
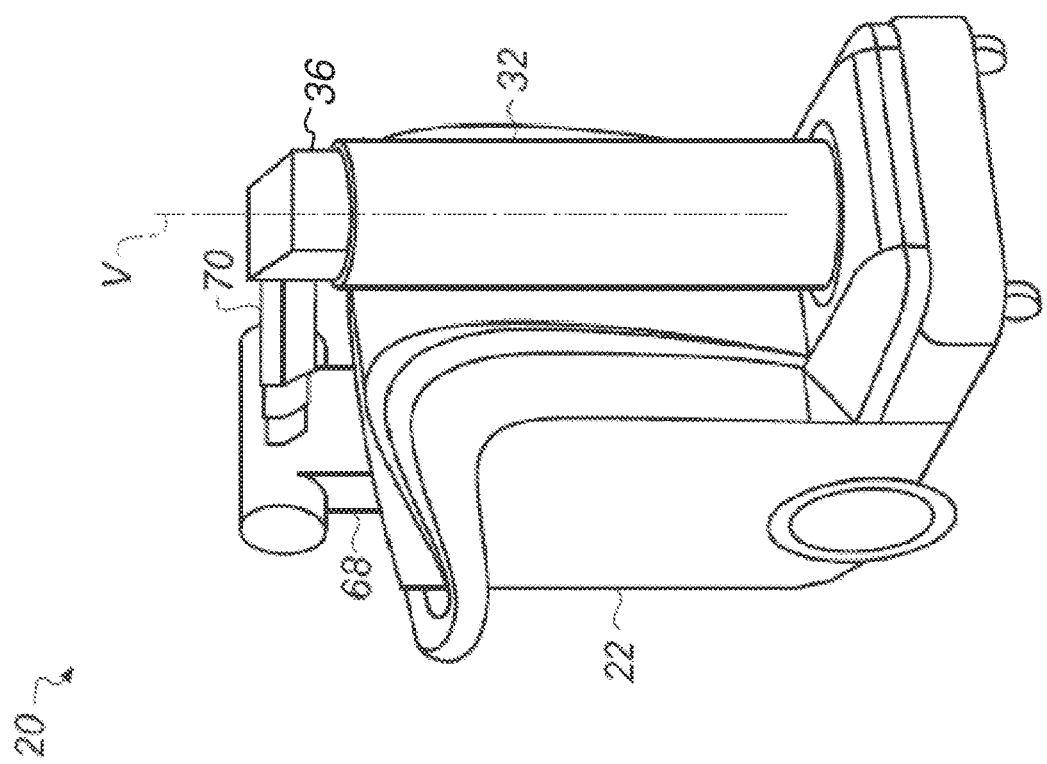
FIG. 4 shows a perspective view of a mobile radiography unit with a sectioned vertical column configured for travel.

The perspective view of FIG. 3 shows a mobile radiography unit 20 that has boom 70 coupled to a sectioned vertical column 30. According to one embodiment, sectioned vertical column 30 includes a movable section 36 telescopically extendable out of, and into, stationary base section 32, which is rotatably attached to transport frame 22. FIG. 3 shows unit 20 with x-ray source 68 in position for imaging, extended outward and supported on boom 70, along a horizontal axis H that is perpendicular to the vertical axis V. FIG. 4 shows unit 20 in an alternate arrangement, configured for travel, with the sectioned vertical column collapsed by lowering movable section 36 into stationary section 32 and with x-ray source 68 nestled against a top surface of the transport frame 22. The side view of FIG. 5 shows unit 20 configured for travel and shows how, using the collapsed column, technician 66 visibility is improved over the conventional fixed vertical column arrangement shown previously in FIGS. 1 and 2.

Figure 6:
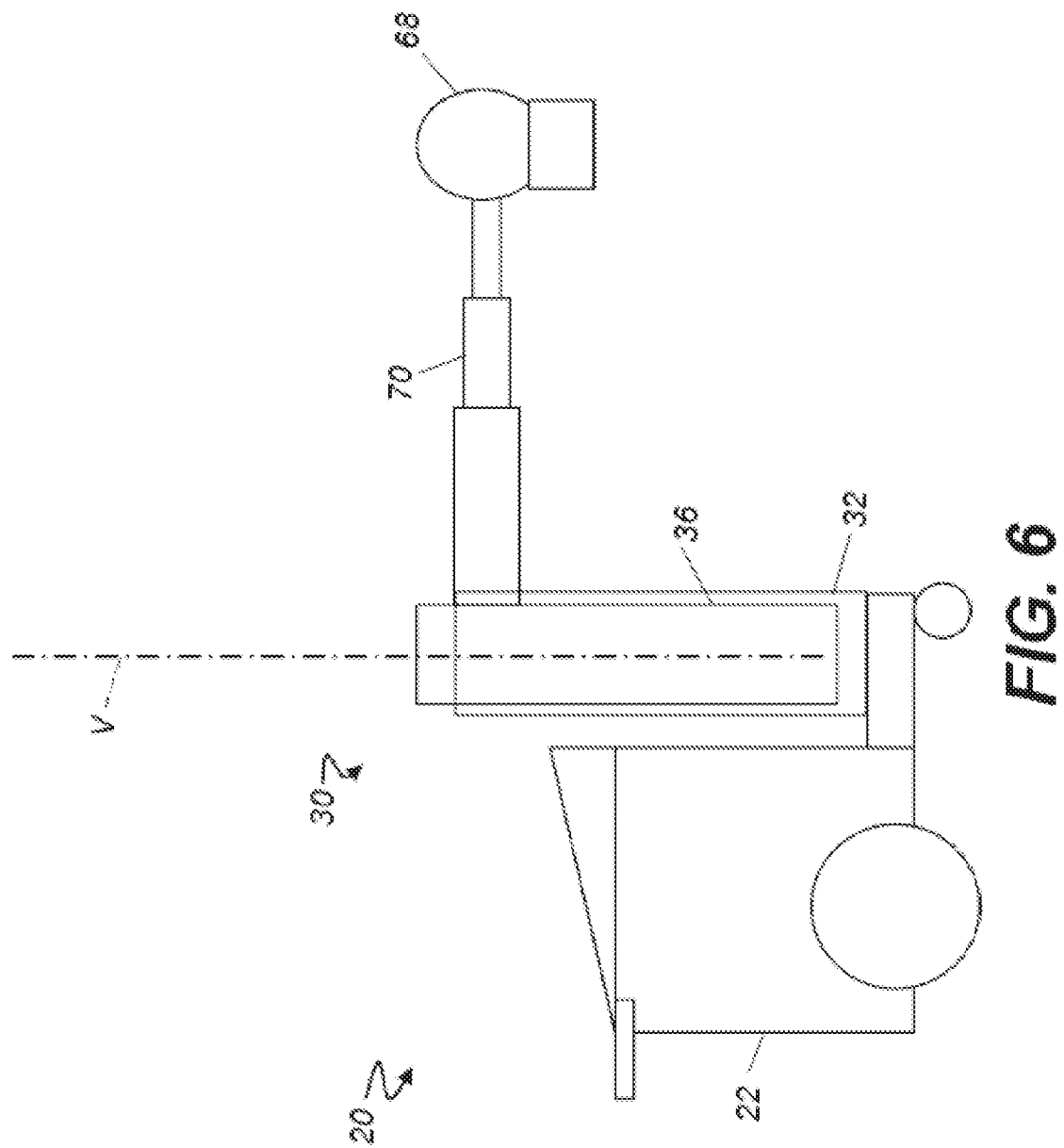
FIG. 6 is a side view showing a mobile radiography unit having a sectioned vertical column in collapsed position.
Figure 7:
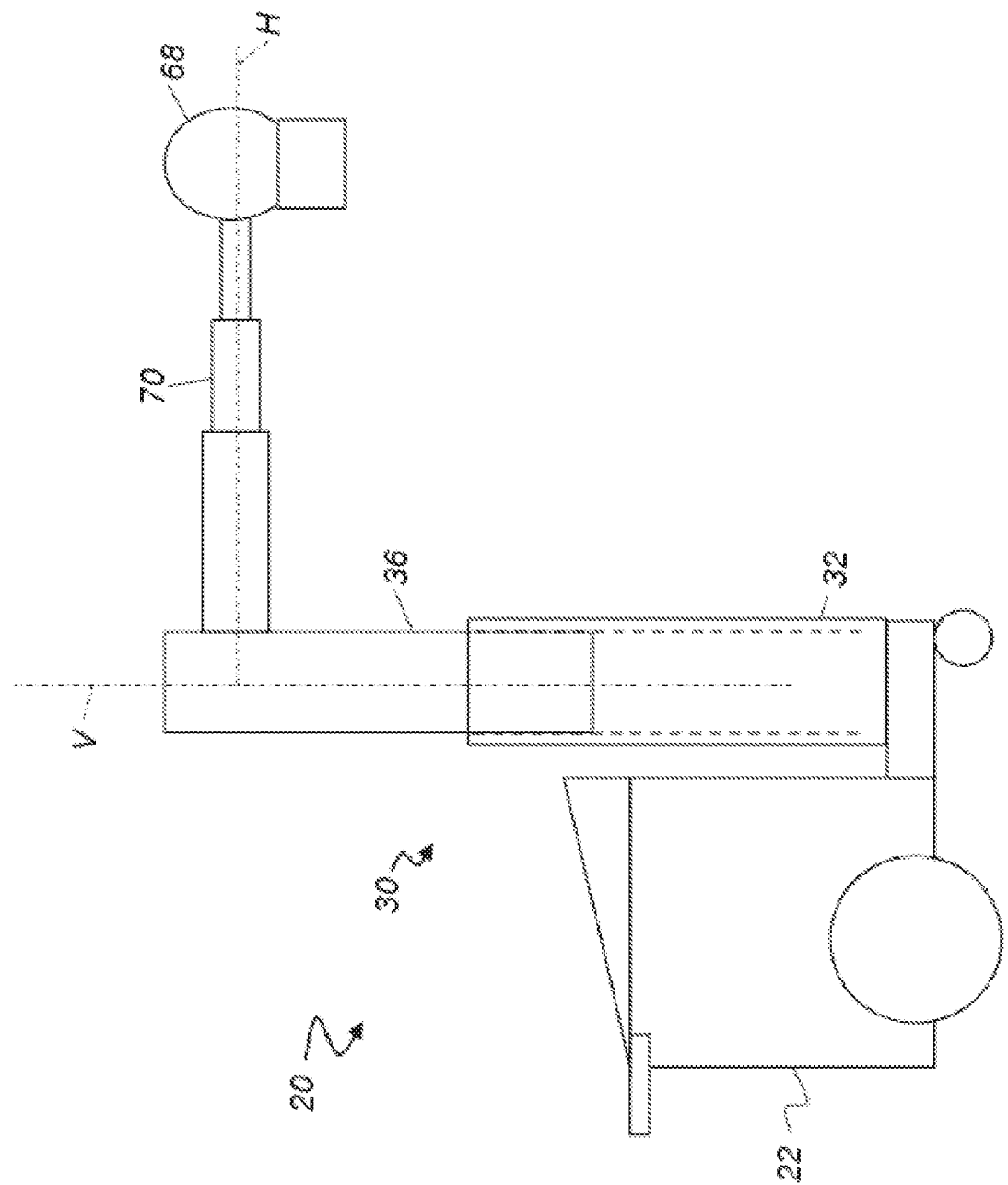
FIG. 7 is a side view showing a mobile radiography unit having a sectioned vertical column that is fully extended for patient imaging.
Figure 8:
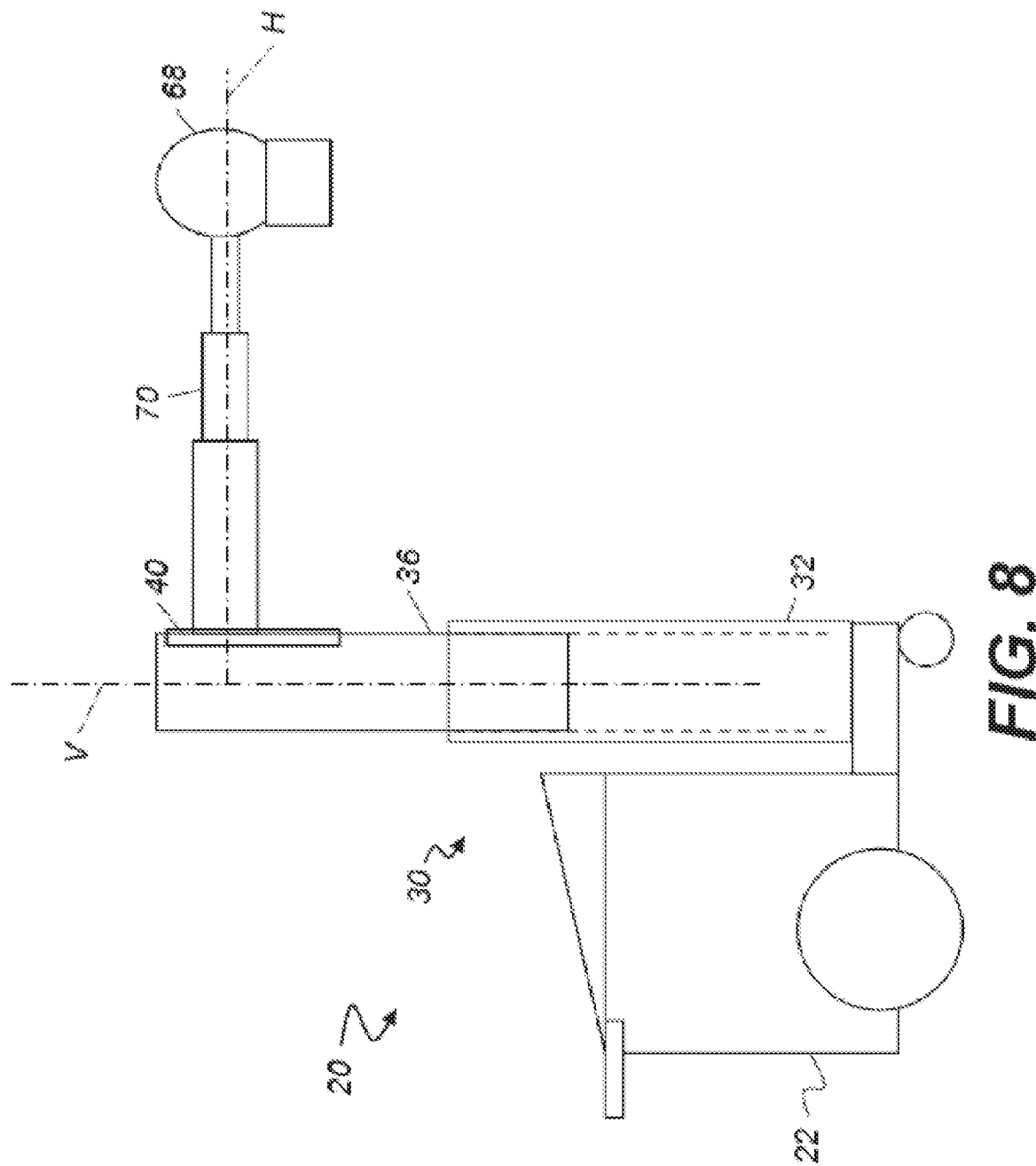
FIG. 8 is a side view showing a mobile radiography unit having a sectioned vertical column that is fully extended for patient imaging with a boom transport mechanism for the x-ray source.

In each of the embodiments shown in FIGS. 6-8, mobile radiography unit 20 has a wheeled transport frame 22 and has display and control panel components needed for operation, as was described previously with reference to FIG. 1. Sectioned vertical column 30, mounted on frame 22, defines a vertical axis V and has a base section 32 that seats against frame 22 and has a first vertical position relative to axis V, which is a fixed vertical position, in one embodiment. One or more movable sections 36 are translatable to extend along the vertical axis V, so that boom 70 can be set to a suitable height over a range of possible height settings. In each embodiment, x-ray source 68 can be set to variable vertical and horizontal positions as well as to a range of angular positions about the vertical axis V.

In the embodiments shown in FIGS. 6 through 21, sectioned vertical column 30 has a single movable section 36. Section 36 is movable in telescoping fashion with respect to stationary base section 32. Boom 70 extends outward from sectioned vertical column 30 and can be rotated at least over some angular range into position about vertical axis V. Rotation about axis V can be achieved in a number of ways. In the embodiments shown in FIGS. 6 through 19D, sectioned vertical column 30 itself rotates in relation to its transport frame 22. In an alternate embodiment, only the movable section 36, with its attached boom 70, rotates. In each of these embodiments, both rotation about vertical axis V and vertical displacement along the vertical axis can be performed simultaneously.

Figure 5:
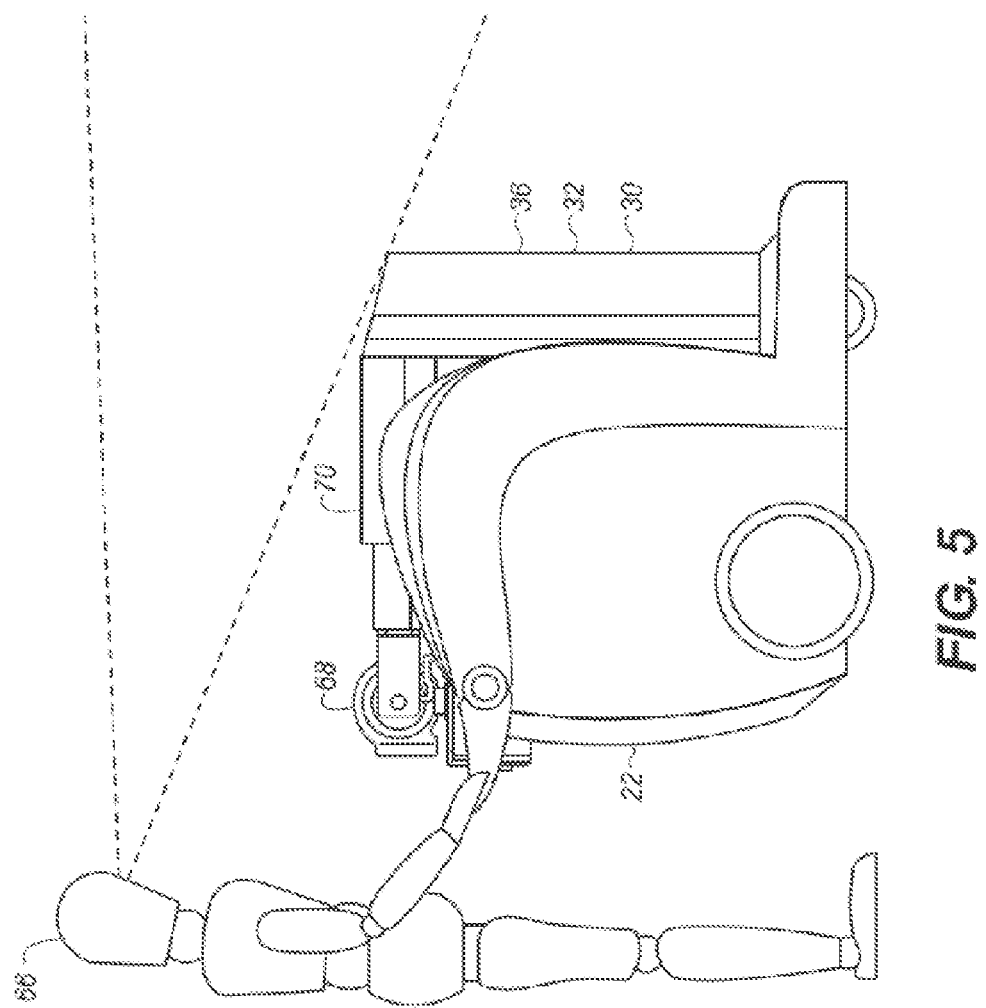
FIG. 5 shows a side view of a mobile radiography unit with a sectioned vertical column according to one embodiment of the present invention.

In the travel configuration of FIG. 5, sectioned vertical column 30 is collapsed and boom 70 is rotated inward in order to seat x-ray source 68 in a stable, docked position for movement, such as for wheeling the entire mobile radiography unit 20 from one patient area to another. FIG. 6 shows initial elevation of sectioned vertical column 30 moved from its travel position and rotated, readying the unit for deployment. FIG. 7 shows vertical column 30 fully extended, with boom 70 facing outward and with movable section 36 at its extreme end of travel, with x-ray boom 70 extended orthogonally outward from sectioned vertical column 30 along horizontal axis H, ready for imaging in this position.

It is beneficial to allow the fullest possible range of vertical heights for the x-ray source in a portable system, from above shoulder height of the imaging technician to relatively low elevations, such as might be beneficial for imaging the foot or ankle of a patient near a floor whereupon the mobile radiography unit 20 is positioned. It can be appreciated that this desired height range presents a problem for telescoped column designs. When a telescoped column is fully collapsed, as shown in FIG. 6, boom 70, when attached in fixed position along movable column section 36, can no longer be moved downward. This movement limitation can make the telescoping arrangement less desirable for portable radiography systems.

Embodiments of the present invention address this difficulty by using a boom transport mechanism that cooperates mechanically with a telescoping, sectioned vertical column to allow displacement of the x-ray boom over a wide range of height settings. Advantageously, the operator can easily adjust x-ray boom height, with the weight of column and boom components mechanically balanced so that a substantially uniform amount of effort is needed for height adjustment to any level within the height range.

Figure 9:
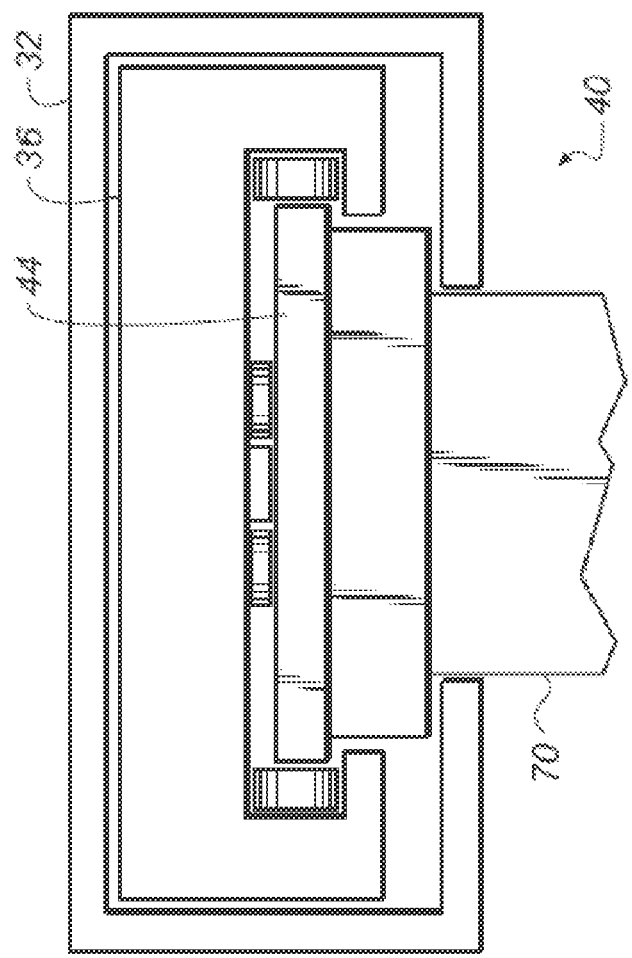
FIG. 9 is a top view cross-section of the sectioned vertical column showing the movable section within the fixed outer base section.

The side views of FIG. 8 and following show an embodiment of mobile radiography unit 20 in which a boom transport mechanism 40 is mounted on movable section 36 and is actuable to provide the added vertical range needed for imaging with source 68 at a low elevation below the range that is typically feasible with sectioned vertical column 30 fully collapsed when using the embodiment shown in FIG. 6. Boom transport mechanism 40 allows a second mode of vertical displacement for boom 70, so that not only is boom 70 mounted on a vertically collapsible column, but its vertical travel is further permitted for a distance along the length of the movable section 36. FIG. 9 shows a top view cross-section of sectioned vertical column 30 in the FIG. 8 embodiment, showing movable section 36, with a carriage 44 as part of boom transport mechanism 40, supporting boom 70 within fixed outer base section 32.

Figure 10:
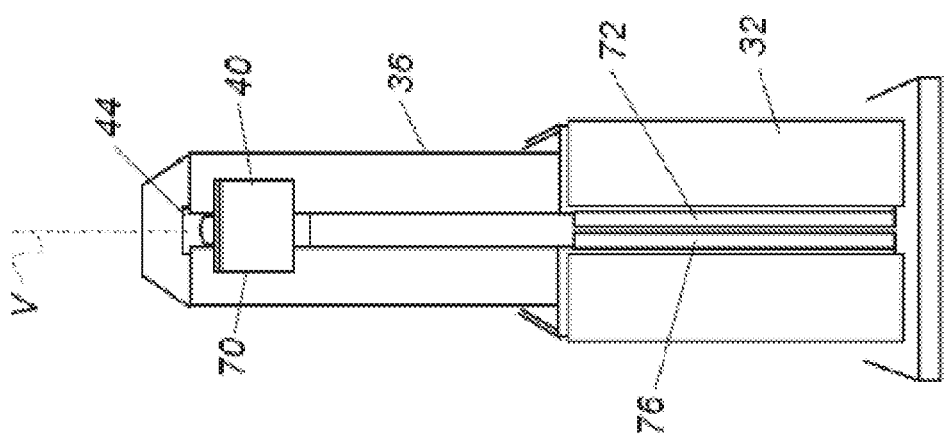
FIG. 10 is a perspective view of the sectioned vertical column of FIG. 8, with boom portions removed for visibility.

FIG. 10 is a perspective view of the sectioned vertical column of FIG. 8, with boom portions removed for better visibility. When movable section 36 travels inside base section 32, a vertical slot 72 is provided in base section 32. Slot 72 allows boom 70 to travel along the length of base section 32 when in the collapsed column configuration. In one embodiment, a sleeve 76, formed from a resilient material such as rubber or plastic or using brushes or other suitable material, provides a protective covering over slot 72 that allows boom 70 travel along the slot 72.

An important design consideration for usability of mobile radiography unit 20 is the ease of movement that is needed for proper positioning of the x-ray source 68 relative to the patient and to the x-ray detector panel. This is a complex mechanical problem due, in part, to the weight of the x-ray tube and its collimator, which can exceed 100 pounds in some systems. The operator should be able to readily move x-ray source 68 to the needed vertical and horizontal position without undue exertion. In addition, the amount of effort needed to adjust the elevation of x-ray source 68 should be balanced over its full range of vertical displacement, so that substantially no additional effort is needed to adjust its height from any level to another.

Figure 11:
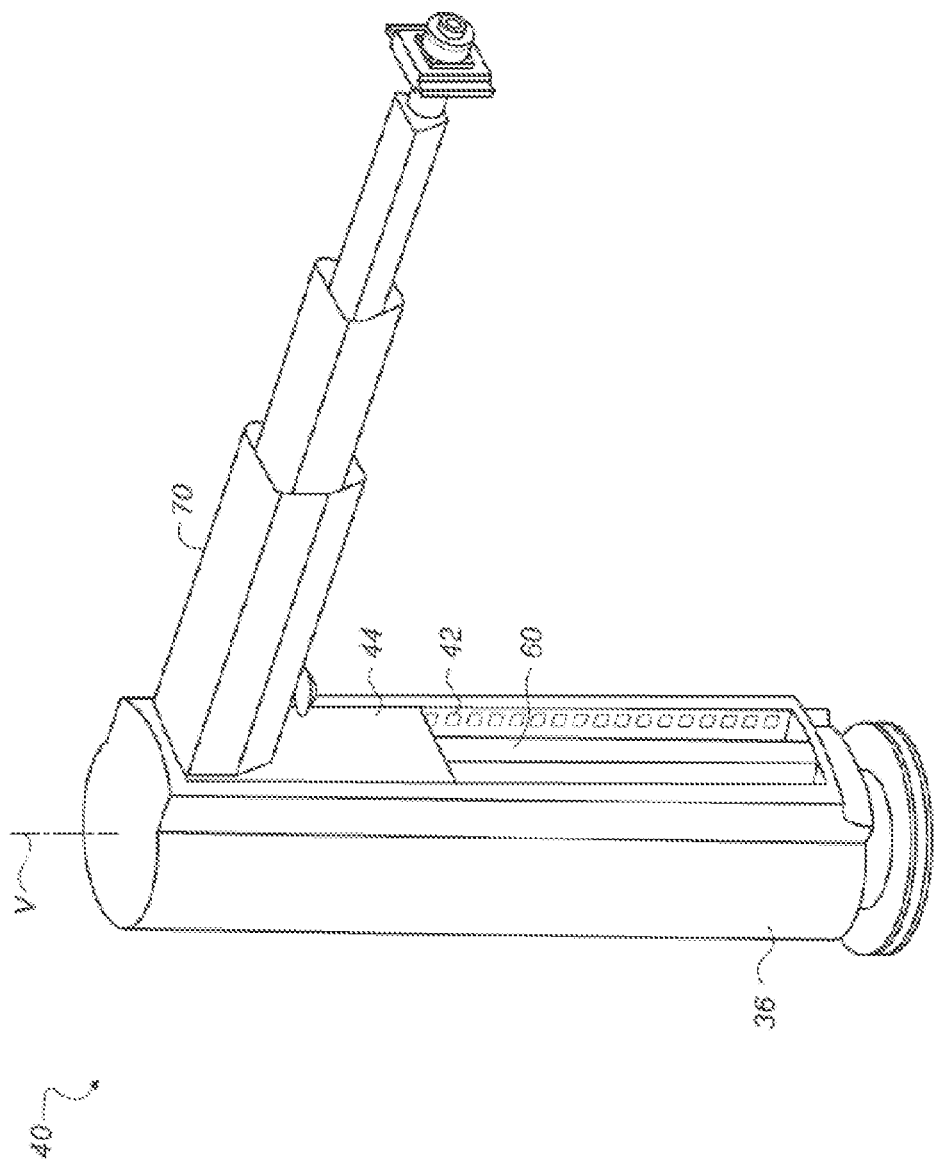
FIG. 11 is a perspective view showing the boom transport on the upper section of the collapsible column, with the transport in an upper position.
Figure 12:
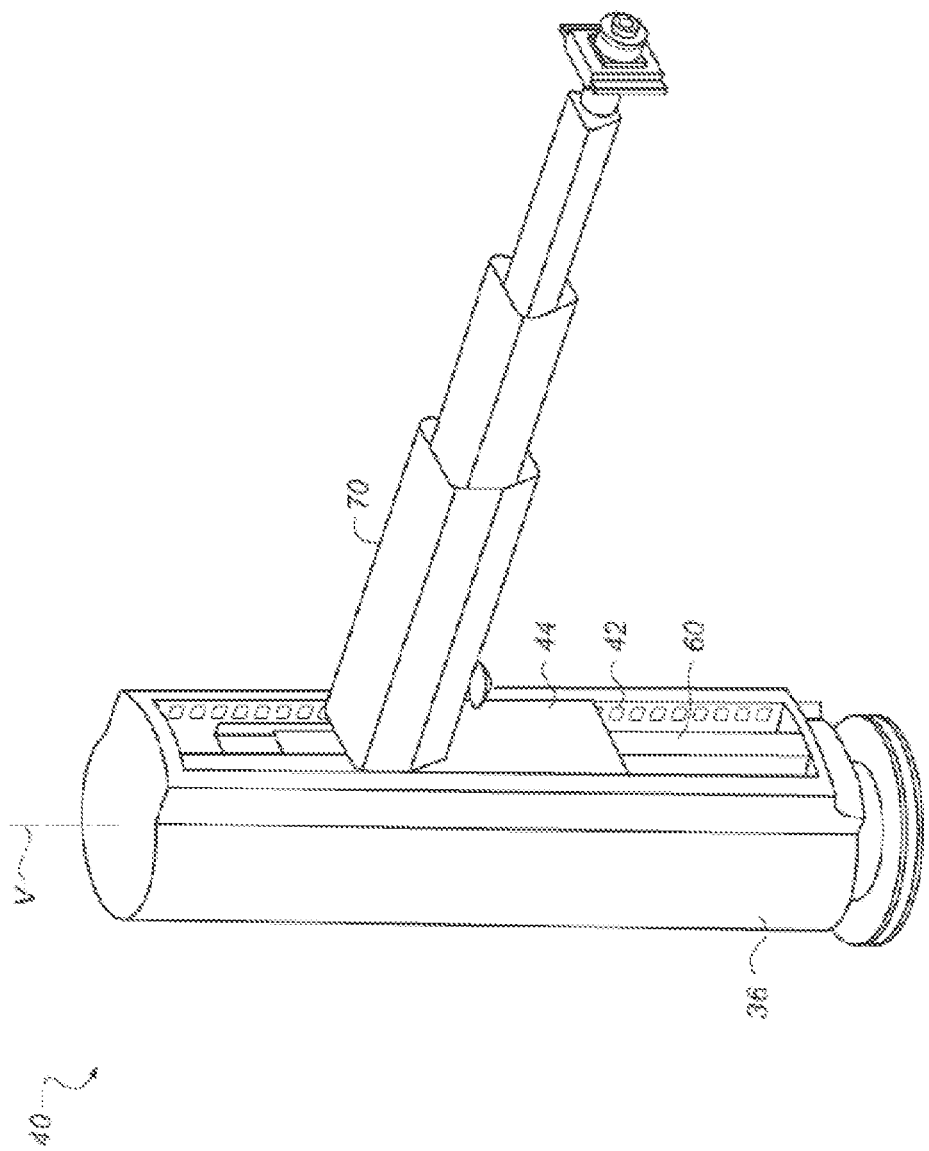
FIG. 12 is a perspective view showing the boom transport on the upper section of the collapsible column, with the transport in a middle position.

The perspective views of FIGS. 11, 12, and 13 show boom transport mechanism 40 and carriage mechanism 44 in different vertical positions along upper movable section 36. In these figures, boom transport mechanism 40 is coupled to section 36 by wheeled carriage mechanism 44 that is movable within a track 42.

Boom transport mechanism 40, shown in schematic detail in top and side views of FIGS. 14A and 14B, respectively, has a series of wheels 54 that rotate within a track 42 to provide vertical displacement. Four wheels are used for this function in the embodiment shown in FIGS. 14A and 14B. Two additional pairs of wheels 58 rotate in an orthogonal direction against a centering block 60 (FIG. 11) in order to constrain unwanted side-to-side movement of boom 70 relative to the vertical axis. It can be appreciated that alternative embodiments can be used for boom transport mechanism movement, including the use of one or more linear bearings and sliders, for example.

Figure 15B:
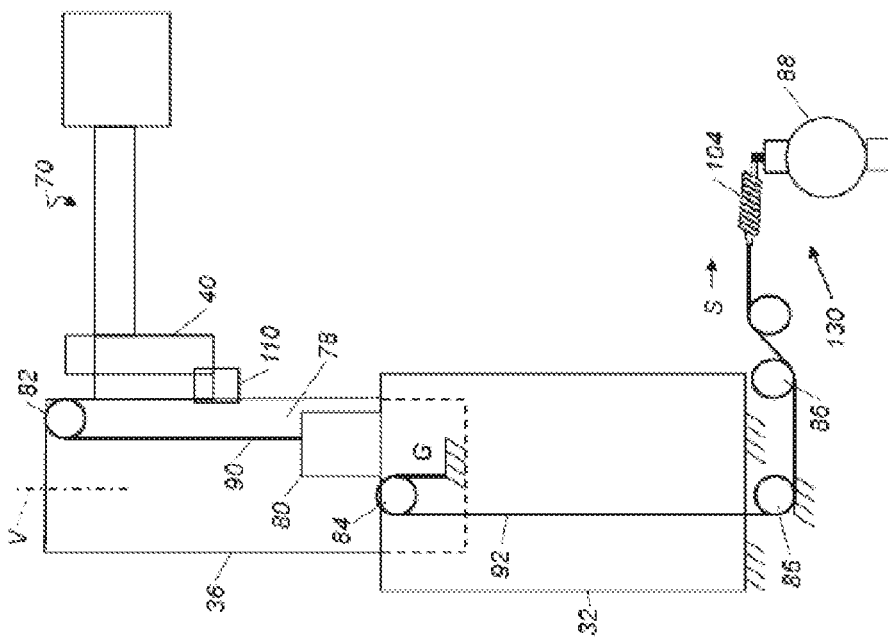
FIGS. 15A and 15B show schematically how a counterweight is deployed in order to provide a lifting force for a boom apparatus in an embodiment of the present invention that uses a sectioned vertical column.
Figure 15A:
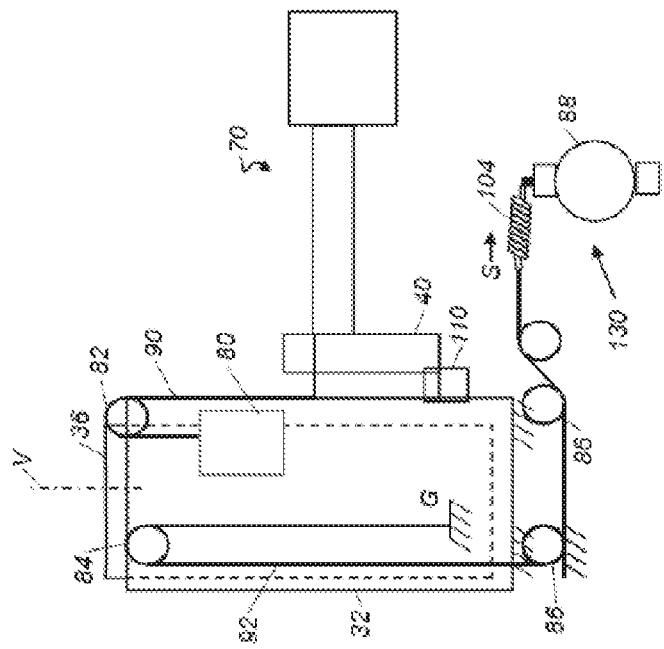

FIGS. 15A and 15B show schematically how a counterweight 80 is deployed in order to provide a lifting force for boom 70 in an embodiment of the present invention that uses a sectioned vertical column. FIG. 15A shows boom 70 at a low elevation, with the section column collapsed, such as might be used for imaging a patient's foot or lower leg, for example. FIG. 15B shows the column in an extended position, with movable section 36 extended from base section 32 and boom 70 raised toward its maximum height. Counterweight 80 is operatively coupled to boom 70 by means of a pulley 82 and a cable 90. In cooperation with boom 70 movement, counterweight 80 is vertically displaced along a shaft 78, a cavity that extends within the column, in the direction of the vertical axis V.

In the embodiment shown in FIGS. 15A and 15B, components of a counterbalance apparatus 130 are shown. A counterbalance force S is provided by a tension force element 104, such as a tension spring, for example. A motor 88 or other actuator provides additional counterbalance force when needed to drive movable section 36 toward a desired vertical position. An optional height sensing element 110 is energizable to provide a signal that is indicative of either or both the column height and/or the vertical position of boom 70 relative to movable section 36. This signal is used to actuate motor 88 when needed, as described in more detail subsequently. To provide a lifting force, a cable 92 is routed around a pulley 84 and through wheels 86 to tension force element 104 and motor 88 or other actuator. A mechanical ground to movable column 36 is shown at G.

Counterweight 80 travels within shaft 78 that is internal to the sectioned column, with the column dimensionally sized for portability. This sets some constraints on the overall width dimension (that is, dimensions orthogonal to the vertical axis V) that can be allowed for this heavy counterweight 80 component, whose weight, and thus the counterweight force available, depends both on its volume and on the mass of its component material. Lead is conventionally used for counterweights, but other materials that are considered less hazardous are preferred and can be used if additional volume is provided. In addition to volume constraints, it is preferable that the operator be shielded from possible inadvertent contact against moving parts such as internal pulleys, cables, and related moving components that relate to boom or column movement.

Figure 16A:
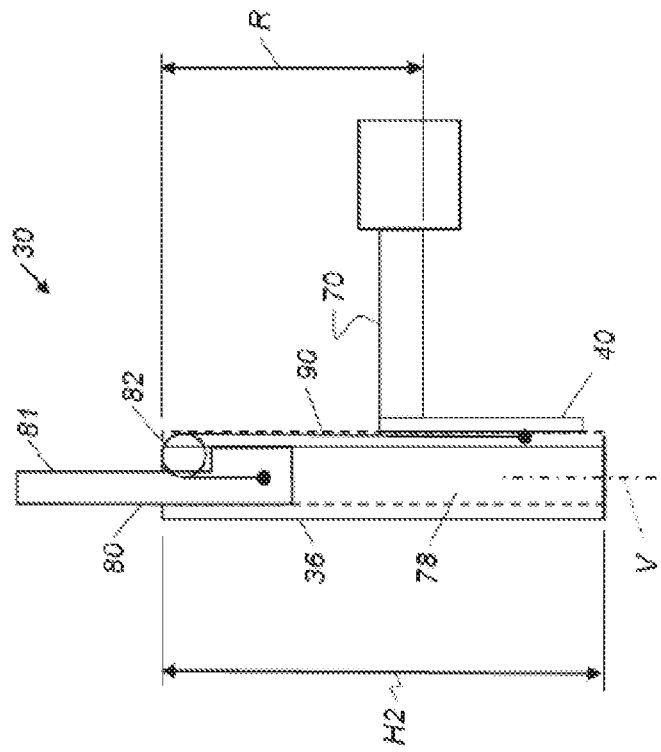
FIGS. 16A and 16B show schematically the use of a counterweight that is elongated, according to one embodiment of the present invention, with the boom apparatus in raised and lowered positions, respectively.
Figure 16B:
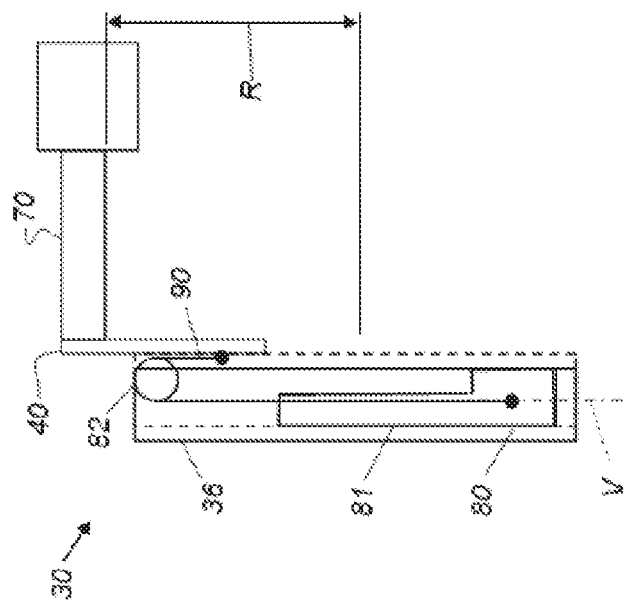
Figure 16D:
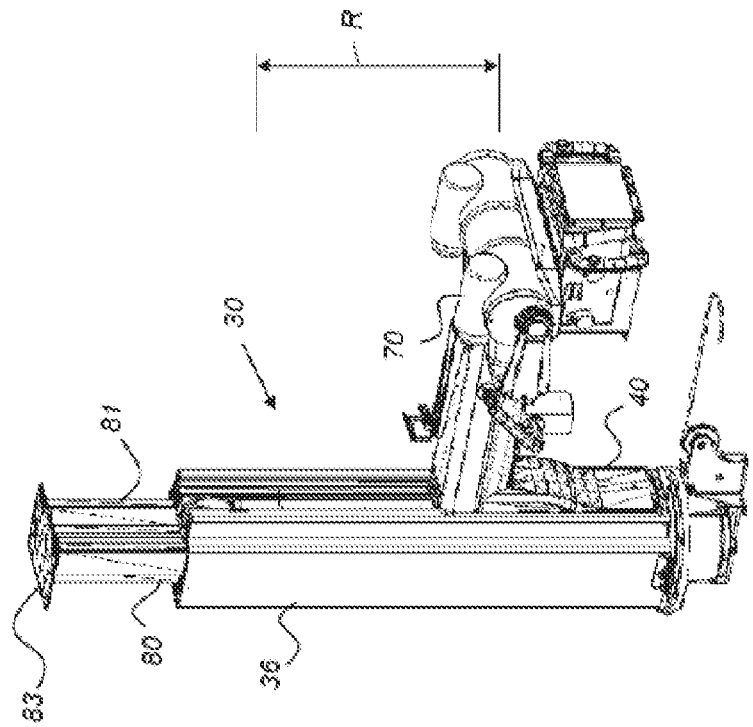
FIGS. 16C and 16D are perspective views that show boom apparatus in the raised and lowered position and show the counterweight element extending upwards when the boom is lowered.
Figure 16C:
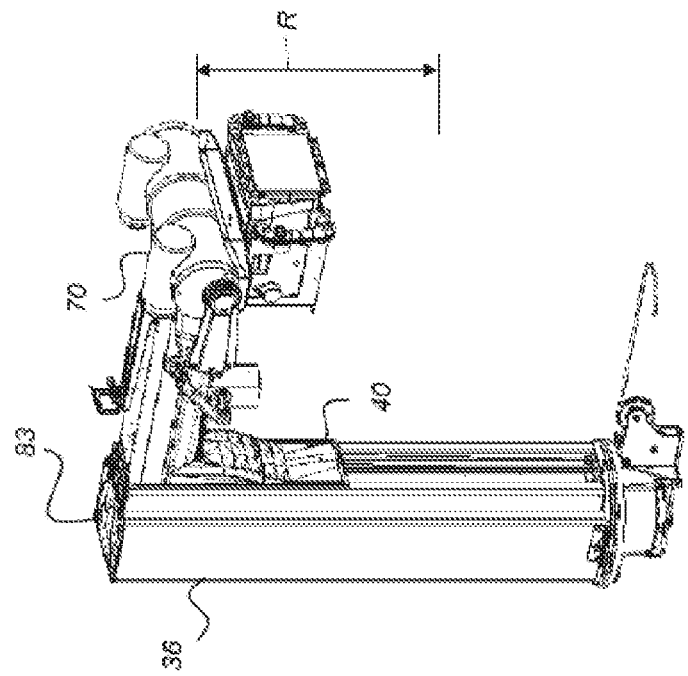

As shown schematically in FIGS. 16A and 16B, and in perspective views in corresponding FIGS. 16C and 16D, embodiments of the present invention address the problem of limited width dimension by extending the length of counterweight 80 in the vertical direction. An extended section 81 adds volume to counterweight 80 in a vertical direction. FIGS. 16A-D also show a range R of boom 70 displacement relative to column section 36. Range R depends on a number of factors, including the height of movable section 36 and the arrangement of boom transport mechanism 40 components. In one embodiment, for example, range R is between 24 and 30 inches.

FIGS. 16A and 16B show vertical column 30 in a collapsed configuration. As shown in FIGS. 16B and 16D, with boom 70 lowered, extended section 81 of counterweight 80 can protrude or extend above shaft 78, whose top edge is defined by a top edge of vertical column 36. An optional cap 83 is provided to cover shaft 78 in the embodiment of FIGS. 16C and 16D. FIG. 16B shows a shaft height H2, in an embodiment in which shaft 78 extends fully through stationary column section 32. In an alternate embodiment, shaft 78 extends only partway through column section 32. In a multi-column section embodiment, the top of shaft 78 is defined by the top edge of the movable column section 36.

FIGS. 17A, 17B, and 17C show sectioned vertical column 30 with vertically stationary base section 32 and movable section 36. As these figures show, the combination of variable column height and variable counterweight 80 position allows a number of possible combinations for achieving the same height H1 for boom 70. In FIG. 17A, for example, movable section 36 is extended upwards and extended section 81 of counterweight 80 protrudes from the top of shaft 78 by a distance D1 when height H1 is achieved. Here, boom 70 is displaced to near the bottom of displacement range R. In FIG. 17B, the same height H1 is reached with movable section 36 somewhat less extended; here, boom 70 is displaced near the middle of its displacement range R and extended section 81 of counterweight 80 protrudes from the top of shaft 78 by a distance D2 that is less than distance D1. In FIG. 17C, the column is collapsed and, with boom 70 at the position shown relative to movable column 36, near the top of its displacement range R, counterweight 80 is wholly enclosed within shaft 78, with no portion protruding above top edge 79. As can be seen from this example, there can be any number of possible arrangements of column and counterweight 80 components used for achieving intermediate heights of boom 70 using sectioned vertical column 30. An optional brake 52, attached to stationary section 32, is also provided that, when actuated, constrains or prevents vertical movement of movable section 36 with respect to stationary section 32.

With respect to FIGS. 15A through 17C, it can be appreciated that other arrangements of component weights and pulley configurations are possible, as described herein below with respect to FIGS. 20-21, as well as mechanical configurations using counterweights or various types of electromechanical or hydraulic actuators, for example. As shown in the examples given above, vertical column 30 can have one or more movable sections to allow variable height. Various types of mechanical brake configurations are also possible and may be provided for helping to stabilize vertical and rotational movement of column sections or of the boom 70 itself.

Adjusting Column Height

As has been described with reference to FIGS. 15A through 17C, proper adjustment of the column 30 height controls the range of vertical movement that is allowed for adjustment of the boom 70 height. There are a number of considerations for setting the column height, including the type of image to be obtained; conditions such as the height of the patient's bed or other support, and the angle of the digital radiographic detector relative to horizontal.

Embodiments of the present invention use different approaches for setting the height of column 30, for example:

(i) Direct operator control. Using this approach, the operator initiates an instruction to alter the height of column 30. This instruction is entered at control panel 612 (FIG. 1) or at a separate switch or control dedicated to this purpose. Using this method, the operator can enter or step to a set height, or hold down a keyboard key or switch until a desired height setting is achieved.

(ii) Automatic height setting according to view type. Using this approach, the operator setup includes specifying the view type of the image, such as an AP chest x-ray, for example. According to one embodiment of the present invention, setting a view type also selects an associated default column height value, so that the radiography system automatically adjusts the column height according to an operator instruction, as part of operator setup for the exposure. This information is entered at control panel 612 (FIG. 1) or using a separate switch or control dedicated to this purpose. Alternately, the operator can enter additional information, including the height of the patient's bed or supporting platform and the angle of the receiver relative to true horizontal or vertical or relative to the collimator on the tube head.

(iii) Assisted operator positioning. Using this approach, the operator manually lifts or lowers the boom to the desired height setting and the column height adjusts accordingly. Using this method allows the operator to ignore the column height setting and to concentrate only on moving the boom and tube head into the correct position. Unlike approaches (i) and (ii), assisted operator positioning requires system interaction with operator movement. The operator instruction that controls the column height setting is thus entered by the operator in urging boom 70 upward or downward and can be detected, for example, by a signal from height sensing element 110. While not a requirement, it is advantageous to provide column height adjustment that is automated to provide smooth, continuous movement of the boom, so that the operator need not exert extra effort when urging boom 70 upward or downward over different parts of the boom movement range.

Figure 18:
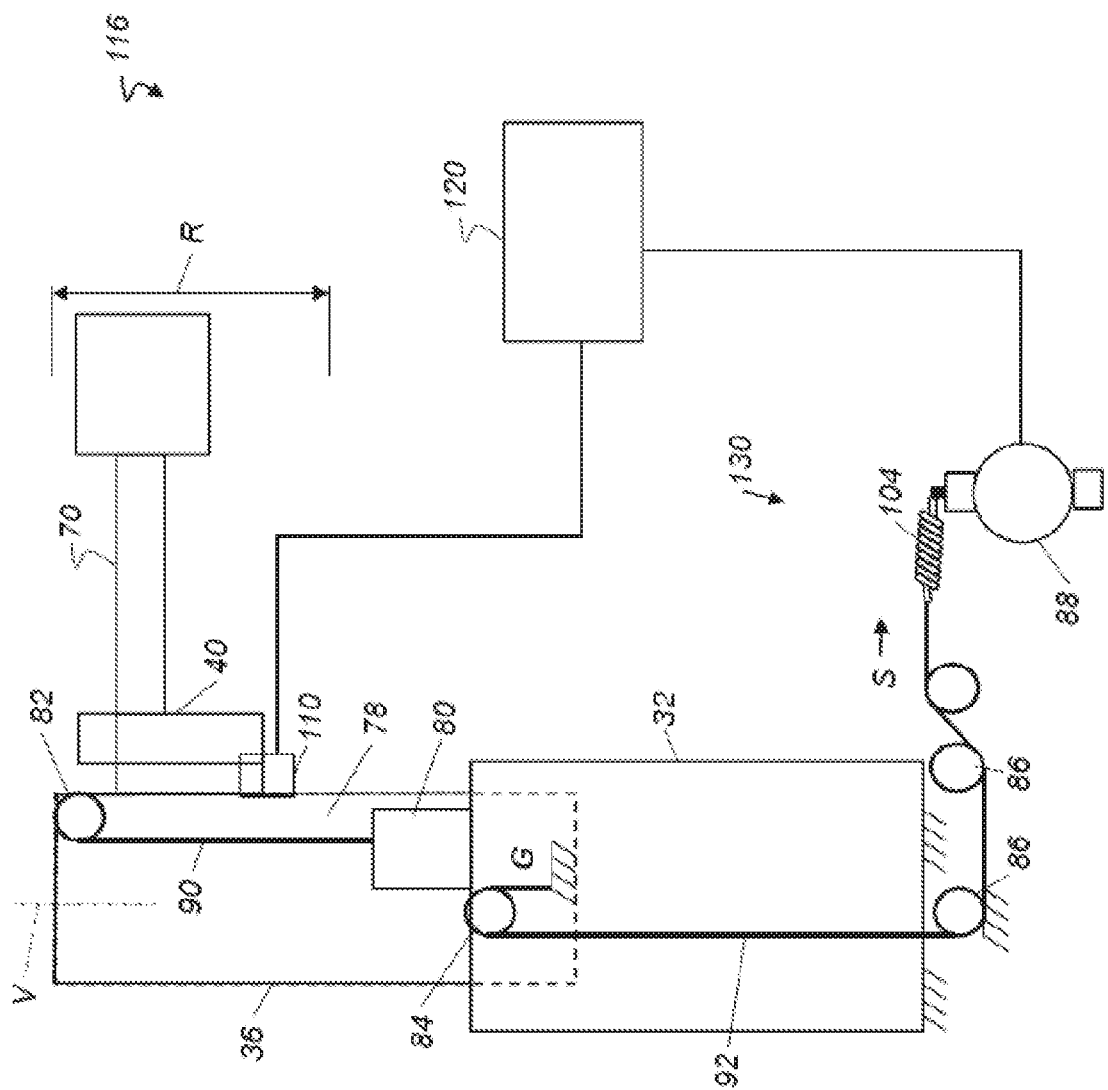
FIG. 18 is a block diagram that shows components of a column height adjustment apparatus according to an embodiment of the present invention.

The schematic block diagram of FIG. 18 shows a column height adjustment apparatus 116 that supports any of approaches (i), (ii), and (iii) listed above in an embodiment of the present invention. A control logic processor 120, which may be a dedicated processor, programmable logic array, or microprocessor, or may be the on-board computer provided for other functions of mobile radiography unit 20, is in signal communication with one or more height sensing elements 110 and with motor 88 or other actuator. Upon receipt of a signal indicating the need for column height adjustment, control logic processor 120 actuates motor 88 to change column height using the system of pulleys 84 and 86, cable 92, and tension force element 104. Where the signal is from direct operator control, as in (i) above, or according to view type for the exposure, as in (ii) above, the signal is obtained from control panel 612, the on-board control logic computer or processor, or other switch.

Column height adjustment for assisted operator positioning, as in (iii) above, is more complex because this requires coordination of column height with boom 70 position. This approach effectively uses boom 70 as the height control used by the operator. As has been noted previously, a goal for ergonomic column movement is to track boom displacement, so that boom 70 is at the extreme ends of displacement range R only when column 30 is either fully extended or fully collapsed. Otherwise, boom 70 moves freely within its displacement range R and the operator can ignore the column 30 height setting. This requires sensing the relative position of boom 70 to movable section 36 and compensating accordingly for boom 70 movement by adjusting column 30 height as a type of "background" operation, without requiring separate operator attention or instructions.

The block diagram of FIGS. 19A and 19B show how counterbalance apparatus 130 supports extension of sectioned vertical column 30 according to one embodiment. FIG. 19A shows the lowest height elevation for boom 70, at the extreme bottom of its displacement range R and with column 30 in its fully collapsed condition. As the operator lifts upward on boom 70, counterbalance apparatus 130 cooperates by providing corresponding extension of column 30. To allow smooth movement of boom 70, control logic processor 120 (FIG. 18) actuates counterbalance apparatus 130 to extend column 30 so that it leads the upward movement of boom 70, acting to effectively center the current boom 70 position with respect to the displacement range R. It is not necessary to precisely reposition range R so that boom 70 is at or near the exact center of range R when moved to a particular height. Some lag or lead distance from exact centering may be appropriate for smooth movement, so that boom 70 does not reach its extreme ends of travel within range R other than when column 30 is at either its maximum extended height or at its minimum collapsed height.

A similar approach to motion control is used for downward movement of boom 70, with slight modification according to an embodiment of the present invention. By way of illustration, FIG. 19C shows boom 70 at its extreme height elevation, at the top of its displacement range R and with column 30 fully extended. As the operator lowers boom 70, control logic processor 120 (FIG. 18) senses this movement and compensates by lowering column 30, again with the goal of effectively centering boom 70 position within displacement range R. Because boom 70 positions the x-ray tube above the patient, however, movement in the downward direction may be slowed compared with movement in the upward direction as was shown in FIG. 19B. Brake 52 may also be actuated for downward movement beyond a certain height or where movement speed, as indicated by height sensing element(s) 110 or other sensor element, exceeds a threshold value.

In the movement sequence described with reference to FIGS. 19A through 19D, motion control logic tracks the relative position of boom 70 in an interactive manner and is able to compensate for height change as well as for the rate of change. To do this requires that control logic processor 120 obtain and respond to updated information on boom 70 position and on column 30 height. In addition, the speed of translation of movable section 36 may change depending on how close boom 70 height is to the upper and lower boundaries of displacement range R. Control solutions for adapting both to changes in relative position and to varying rates of change in position, and for providing smooth motion in performing this compensation, are well known to those skilled in the motion control arts.

There are numerous ways to sense boom 70 displacement within its range R as well as column 30 height, using continuous or discrete sensors of various types, as is well known to those skilled in the motion control arts. In one embodiment, the sensor used as height sensing element 110 is a linear detection element, such as a linear encoder, that generates a signal that is indicative of boom 70 height with respect to column 30 or within displacement range R. This signal continually updates position information for control logic processor 120. Column 30 height is determined by motor driver logic, according to one embodiment. In an alternate embodiment, multiple sensor elements are used as height sensing elements 110, such as to indicate boom 70 position near each end of travel within range R. Discrete sensors for height sensing element 110 can alternately be limit switches or other switch elements positioned at various set-points for both boom 70 travel and column 30 height. A rotary encoder could alternately be used as height sensing element 110.

Figure 20:
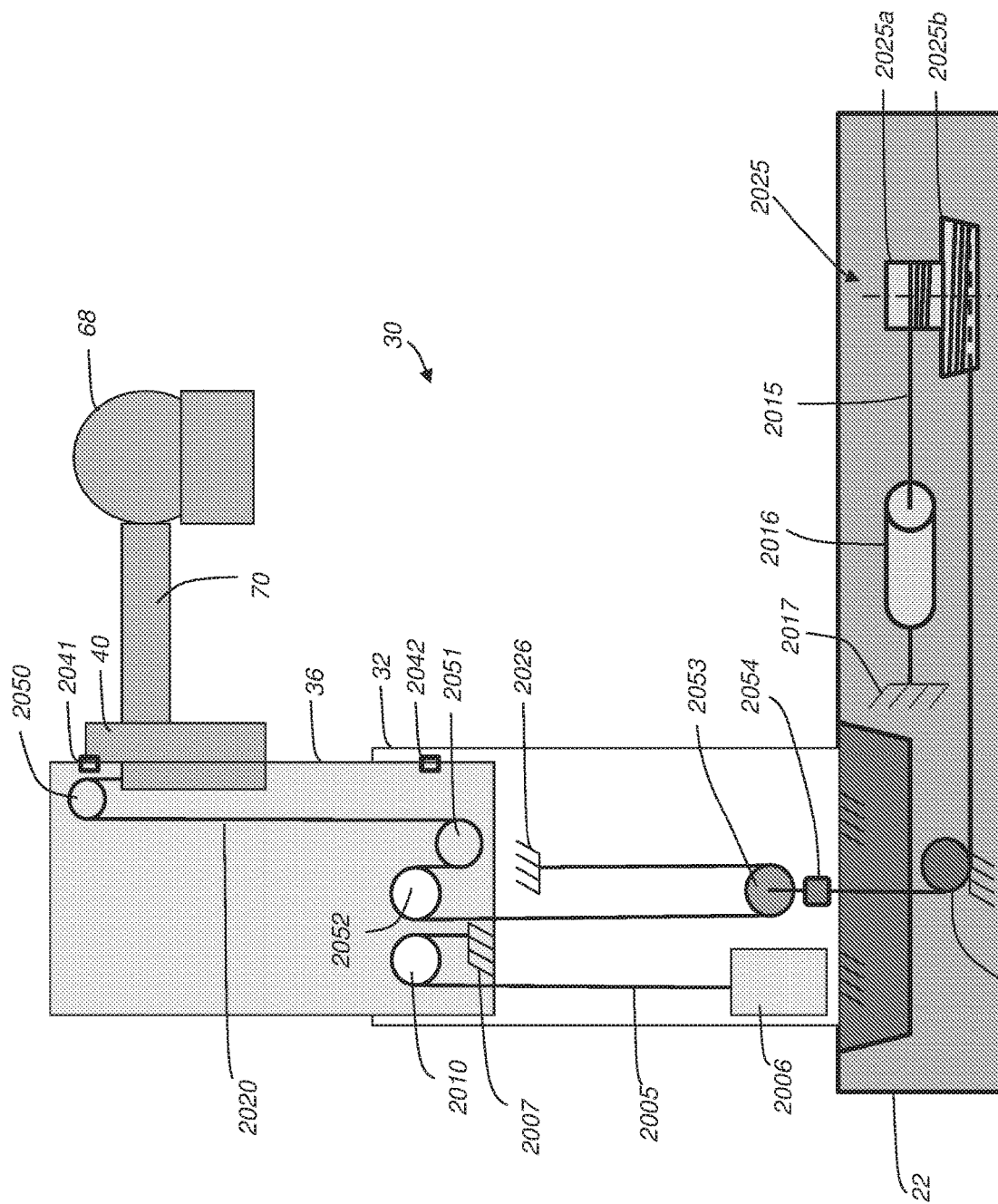
FIG. 20 is a schematic block diagram of a boom apparatus on a portion of a sectioned vertical column using a novel assembly of cables, pulleys, and spring to assist vertical positioning.
Figure 21:
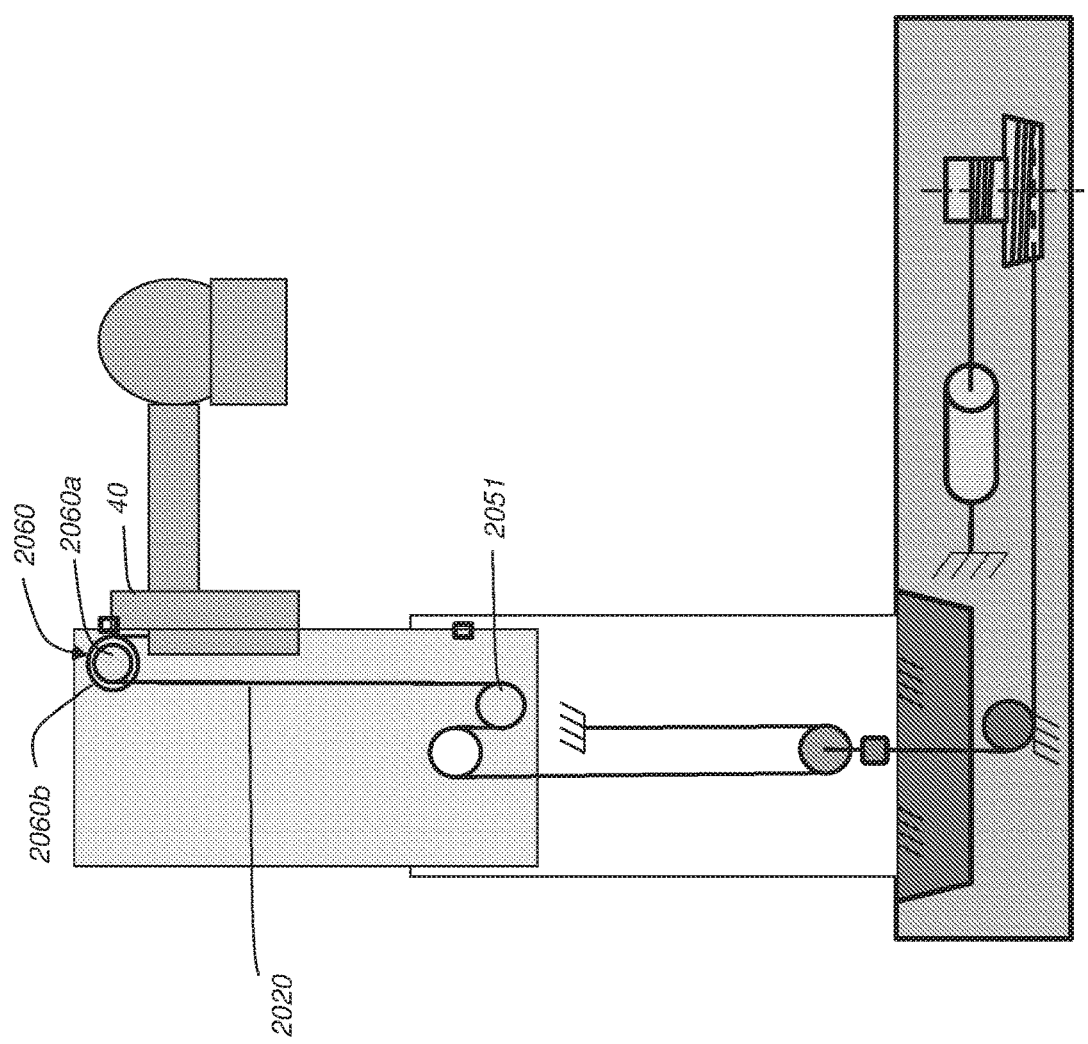
FIG. 21 is a schematic block diagram of a boom apparatus on a portion of a sectioned vertical column using another novel assembly of cables, pulleys, and spring to assist vertical positioning.

FIG. 20 is a schematic diagram of a mechanical assist assembly disposed within the vertical column sections 32, 36, and within a housing of the transport frame 22. The mechanical assist assembly may include up to three cable and pulley systems as described herein, including movable and fixed pulley cable systems and a tension adjustment element, such as a spring. A first cable and pulley system uses a cable 2020 having one end attached to the boom transport mechanism 40 at an upward facing portion thereof, and an opposite end attached, or anchored, to the base section 32 of the vertical column 30 at a cable ground 2026 affixed on an interior surface thereof. The fixed and movable pulleys as described herein may have an annular groove along a circumference of a rotatable wheel to guide a cable, belt, chain or rope looping around the pulleys. The wheel and groove portion of the fixed pulleys described herein rotate about a fixed stationary center shaft coinciding with a central rotational axis of the pulleys. These center shafts of the fixed pulleys may be attached to a part of the vertical column 30 or transport frame 22, allowing the wheel of the pulleys to rotate around a fixed axis.

As shown in FIG. 20, the cable 2020 extends upward from its attachment to the boom transport mechanism 40 then loops downward around fixed pulley 2050, attached by its central shaft to the movable column section 36 on an interior surface thereof, then loops upward around fixed pulley 2051, also attached by its central shaft to the movable column section 36 on an interior surface thereof, then loops downward around fixed pulley 2052, attached by its central shaft to the base column section 32 on an interior surface thereof, and then loops upward around movable floating pulley 2053 to the cable 2020 anchor point 2026, affixed on an interior surface of the base section 32 of vertical column 30, as shown in FIG. 20. The first cable and pulley system just described may be said to be disposed within the vertical column 30 of the mobile radiography apparatus.

A second cable and pulley system, cooperating with the first cable and pulley system using cable 2020, uses a cable 2015 having one end attached to the floating and movable pulley 2053, and an opposite end attached, or anchored, to the transport frame 22 at a cable ground 2017 affixed thereto on an interior surface thereof. The cable 2015 travels downward from the floating pulley 2053 into the transport frame section 22, then loops transversely outward, at an angle of about 90° from its downward portion, around fixed pulley 2024 attached by its central shaft to a fixed interior portion in the transport frame 22. Cable 2015 then loops around a tapered wide portion of a dual radius fixed pulley 2025 attached by its central shaft to the transport frame section 22 on an interior surface thereof. Then the cable 2015 extends from the tapered dual radius fixed pulley 2025 in a direction back toward fixed pulley 2024 and is attached to one end of a tension adjustment member 2016, such as a spring. Another section of cable 2015 is attached to a second end of tension adjustment member 2016 and then to the cable 2015 anchor point 2017 affixed on an interior surface of the transport frame 22, as shown in FIG. 20.

The tapered dual radius fixed pulley 2025 comprises a smaller radius portion 2025a whereabout the cable 2015 loops and continues to the adjustable tension member 2016. The tapered dual radius fixed pulley 2025 comprises a tapered wide radius portion 2025b whereabout the cable 2015 loops and continues to the fixed pulley 2024. The tapered larger radius portion 2025b of the tapered dual radius fixed pulley 2025 comprises a tapered radius portion that provides a continuously variable radius for the cable 2015 that loops around it. The smallest radius of the larger tapered radius portion 2025b of the dual radius fixed pulley 2025 may be greater than the radius of the smaller radius portion 2025a of the dual radius fixed pulley 2025. The dual radius fixed pulley 2025 may be configured to guide a single continuous cable or, in an alternative embodiment, two cable sections. In a two cable section embodiment, a section of cable 2015 that extends to fixed pulley 2024, may loop around and be anchored to the larger tapered radius portion 2025b of the fixed dual radius pulley 2025, and a second separate section of cable 2015 may extend from the adjustable tension member 2016 and loop around and be anchored to the smaller radius portion 2025a of the fixed dual radius pulley 2025. In a single cable embodiment, one continuous cable 2015 loops around both the smaller and larger radius portions 2025a, 2025b, of the dual radius fixed pulley 2025. The single cable embodiment typically requires the cable 2015 to be clamped, or anchored, to the dual radius fixed pulley 2025 at a selected location between the two pulley radius portions 2025a, 2025b. The second cable and pulley system just described may be said to be disposed within the transport frame section 22 of the mobile radiography apparatus, except for the portion of cable 2015 that travels into the base section 32 for attachment to the movable floating pulley 2053.

A third cable and pulley system, cooperating with the first and second cable and pulley systems described above, uses a cable 2005 having one end attached to a counterweight 2006 and an opposite end attached, or anchored, to the movable column section 36 at a cable ground 2007 affixed thereto on an interior surface thereof. The cable 2005 travels upward into the movable column section 36 from the counterweight 2006 then loops downward around fixed pulley 2010 attached by its central shaft to the base section 32 on an interior surface thereof, and then to its anchor point 2007, as shown in FIG. 20. The third cable and pulley system just described may be said to be disposed within the vertical column 30 of the mobile radiography apparatus.

An alternative swivel 2054 may be used to connect the cable 2015 to the movable pulley 2053. The swivel is connected on one side to an end of a first portion of the cable 2015, and is connected on a second side to a second portion of the cable 2015. The swivel 2054 allows the movable pulley 2053 and the cable 2015 to freely rotate with respect to each other about an axis coinciding with a vertical length of the cable 2015 proximate the swivel 2054.

An alternative embodiment to the mechanical assist assembly described herein above is illustrated in the schematic diagram of FIG. 21. FIG. 21 is a schematic diagram of a mechanical assist assembly disposed within the vertical column 30 and within a housing of the transport frame 22 as described above in relation to the embodiment of FIG. 20, except that the third cable and pulley system, comprising counterweight 2006, cable 2005, fixed pulley 2010, and cable ground 2007 (all shown in FIG. 20), is not included, and a dual-radius (non-tapered) fixed pulley 2060, having small radius portion 2060a and larger radius portion 2060b, replaces fixed pulley 2050 (FIG. 20). For ease of reference, not all the elements of FIG. 21 are labeled with numerals, however, operation and structure of relevant elements are described with reference to FIG. 20 herein above. As explained herein above with respect to dual radius pulley 2025, the dual radius fixed pulley 2060 may also be configured as a single continuous cable or two cable section pulley. In a two cable section embodiment, a cable, such as the section of cable 2020 that extends to dual radius pulley 2060 from pulley 2051, may loop around and be anchored to the smaller radius portion 2060a of the fixed dual radius pulley 2060, and a second separate portion of cable 2020 may extend from a top surface of the boom transport mechanism 40 and loop around and be anchored to the larger radius portion 2060b of the fixed dual radius pulley 2060. In a single cable embodiment, one continuous cable 2020 loops around both the smaller and larger radius portions, 2060a and 2060b, respectively, of the dual radius fixed pulley 2060. The single cable embodiment typically requires the cable 2020 to be clamped, or anchored, to the dual radius fixed pulley 2060 at a selected location between the two pulley radii. The portion of cable 2020 looping around the smaller radius portion 2060a of dual-radius fixed pulley 2060 travels downward and around fixed pulley 2051, and the portion of cable 2020 looping around the larger radius portion 2060b of dual-radius fixed pulley 2060 travels downward and is attached to the boom transport mechanism 40 at an upward facing portion thereof, as it does in the embodiment of FIG. 20.

Exemplary vertical movement of the boom 70, using the mechanical assist assemblies described herein, will now be briefly described. In the embodiments of the present invention as illustrated in FIGS. 20-21, the movement of the boom 70, relative to the movable column section 36, and the movement of the movable column section 36, relative to the stationary column section 32, are the same. In the embodiment of FIG. 20, the counterweight 2006 is selectively weighted, or sized, to balance the movable column section 36. With respect to boom 70 and movable column section 36 movement, as the boom 70 is manually raised by an operator the movable column section 36 moves together with the boom 70 until eventually the movable column section 36 reaches a maximum height in its movement along stationary column section 32, whereby further upward urging of the boom 70 by the operator then causes the boom 70 to move upward within, and relative to, movable column section 36, but only if the boom 70 is not already at its maximum height along the movable column section 36, until boom 70 reaches its maximum height along movable column section 36. The balancing force provided by counterweight 2006 assists in easing the force required from the operator to raise the movable column section 36 in this manner. The balancing force provided by counterweight 2006 also assists in preventing downward freeplay movement of the movable column section 36 due to gravity.

As the boom 70 is manually lowered by an operator the movable column section 36 moves together with the boom 70 until eventually the movable column section 36 reaches a minimum height in its movement along stationary column section 32, whereby further downward urging of the boom 70 by the operator then causes the boom 70 to move downward within, and relative to, movable column section 36, but only if the boom 70 is not already at its minimum height along the movable column section 36, until boom 70 reaches its minimum height along movable column section 36. The balancing force provided by counterweight 2006 assists in easing the force required from the operator to raise the movable column section 36 in this manner. The balancing force provided by counterweight 2006 assists in preventing the movable column section 36 from free falling, due to gravity, after a manual downward urging from the operator in this manner.

In one embodiment, upper and lower latches, 2041, 2042, respectively, may be provided by attachment to the movable column section 36. These latches 2041, 2042, may be configured to be manually engageable and releasable by the operator, or they may be electromechanically programmably controlled. The upper latch 2041, when engaged to the boom 70, locks the boom 70 at its highest point of movement along movable column section 36, whereby upward or downward urging of the boom 70 by the operator causes the movable column section 36 to move upward or downward, respectively, between its maximum and minimum heights along the stationary column section 32, while the boom 70 remains stationary relative to the movable column section 36. The lower latch 2042, when engaged to the boom 70, locks the boom 70 at its lowest point of movement along movable column section 36, whereby upward or downward urging of the boom 70 by the operator causes the movable column section 36 to move upward or downward, respectively, between its maximum and minimum heights along the stationary column section 32, while the boom 70 remains stationary relative to the movable column section 36. When the mobile radiography unit 20 is collapsed into a docked position for transport, or is being maneuvered into the docked position, such as shown in FIG. 4, the boom 70 is typically latched at the top of movable column section 36 using latch 2041.

As the boom 70 is manually urged downward, the movable floating pulley 2053 travels upward and the tension adjustment member 2016, such as a spring, is stretched, or elongated; and the movable floating pulley 2053 travels downward and the tension adjustment member 2016, such as a spring, is shortened when the boom 70 is manually urged upward. The larger tapered radius portion 2025*b* of the tapered dual radius fixed pulley 2025 counteracts the increased tension exerted by the tension adjustment member 2016, as it is elongated, so as to maintain, as much as possible, a constant tension force transmitted through cable 2015 to floating movable pulley 2053 in order to balance the weight the the boom 70 as it moves along the movable column section 36. The constant tension maintenance through cable 2015 is achieved by unwinding cable 2015 at an increasing radius from around the tapered radius portion 2025*b* as the tension adjustment member 2016 is elongated, and winding cable 2015 at a decreasing radius around the tapered radius portion 2025*b* as the tension adjustment member 2016 is shortened. The size of the tension adjustment member 2016, and thereby the force it exerts on cable 2015, as well as the radial dimensions of the tapered dual radius fixed pulley 2025 may be selectively designed according to the overall weights and dimensions of the operable components of the mobile radiography system as described herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A mobile radiography system comprising:
   a transport frame having wheels attached thereto for rollably transporting the system, the transport frame having a housing to enclose at least a portion of the system;
   a sectioned vertical column mounted on the transport frame about a vertical axis, the sectioned vertical column comprising:
      a base section supported by and attached to the transport frame, the base section remaining vertically stationary with respect to the vertical axis; and
      a movable upper section, coupled to the base section, that is movable parallel to the vertical axis relative to the base section;
   a boom having a first end movably attached to the movable upper section and extending transversely therefrom, the boom further having an x-ray source attached to a second end thereof opposite the first end, the boom configured to move parallel to the vertical axis and relative to the movable upper section; and
   a column cable and pulley system comprising:
      a column cable having a first end attached to the boom and a second end attached to the base section;
      a floating column pulley within the base section around which the column cable is looped; and
      a frame cable and pulley system comprising a frame cable having a first end attached to the floating column pulley and a second end attached to the transport frame.

2. The system of claim 1, wherein the column cable and pulley system further comprises a first column fixed pulley having a dual-radius attached to the movable upper section around which the column cable is looped.

3. The system of claim 2, wherein the column cable and pulley system further comprises a second column pulley attached to the movable upper section around which the column cable is looped.

4. The system of claim 3, wherein the column cable and pulley system further comprises a third column pulley attached to the base section around which the column cable is looped.

5. The system of claim 1, wherein the frame cable and pulley system is enclosed by the housing of the transport frame.

6. The system of claim 5, wherein the frame cable and pulley system further comprises a first frame pulley attached to the transport frame around which the frame cable is looped.

7. The system of claim 6, wherein the frame cable and pulley system further comprises a second frame pulley attached to the transport frame around which the frame cable is looped.

8. The system of claim 7, wherein the frame cable and pulley system further comprises a tension adjustment member attached to the frame cable between the second frame pulley and the second end of the frame cable.

9. The system of claim 8, wherein the second frame pulley comprises a dual-radius frame pulley.

10. The system of claim 9, wherein a larger radius portion of the dual-radius frame pulley comprises a tapered radius having a continuously variable radius.

11. The system of claim 10, wherein a largest radius of a smaller radius portion of the dual-radius frame pulley is less than a smallest radius of the tapered radius.

12. A mobile radiography system comprising:
a transport frame having wheels attached thereto for rollably transporting the system, the transport frame having a housing to enclose at least a portion of the system;
a sectioned vertical column mounted on the transport frame about a vertical axis, the sectioned vertical column comprising:
a base section supported by and attached to the transport frame, the base section remaining vertically stationary with respect to the vertical axis; and
a movable upper section, coupled to the base section, that is movable parallel to the vertical axis relative to the base section;
a boom having a first end movably attached to the movable upper section and extending transversely therefrom, the boom further having an x-ray source attached to a second end thereof opposite the first end, the boom configured to move parallel to the vertical axis and relative to the movable upper section; and
a column cable and pulley system comprising a column cable having a first end attached to the boom and a second end attached to the base section,
wherein the column cable and pulley system further comprises a first column fixed pulley having a single radius attached to the movable upper section around which the column cable is looped, and wherein the mobile radiography system further comprises a counterweight cable and pulley system comprising a counterweight cable having a first end attached to a counterweight and a second end attached to the movable upper section.

13. The system of claim 12, wherein the counterweight cable and pulley system is entirely disposed within the sectioned vertical column.

14. The system of claim 12, wherein the counterweight cable and pulley system further comprises a counterweight pulley attached to the base section around which the counterweight cable is looped.

15. The system of claim 14, wherein the column cable and pulley system and the counterweight cable and pulley system are both entirely disposed within the sectioned vertical column.

16. The system of claim 12, wherein the column cable and pulley system is entirely disposed within the sectioned vertical column.

17. The system of claim 16, wherein the base section is rotatable about the vertical axis relative to the transport frame.

* * * * *